US012806179B2

(12) United States Patent
Muraoka et al.

(10) Patent No.: US 12,806,179 B2
(45) Date of Patent: Nov. 24, 2026

(54) COMBINATION THERAPY FOR CANCER USING AZABICYCLIC COMPOUND AND POLY(ADENOSINE 5'-DIPHOSPHATE-RIBOSE) POLYMERASE INHIBITOR

(71) Applicant: TAIHO PHARMACEUTICAL CO., LTD., Chiyoda-ku (JP)

(72) Inventors: Hiromi Muraoka, Tsukuba (JP); Naoki Arimura, Chiyoda-ku (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 1118 days.

(21) Appl. No.: 17/633,128

(22) PCT Filed: Aug. 5, 2020

(86) PCT No.: PCT/JP2020/030017

§ 371 (c)(1),
(2) Date: Feb. 4, 2022

(87) PCT Pub. No.: WO2021/025065

PCT Pub. Date: Feb. 11, 2021

(65) Prior Publication Data

US 2022/0280489 A1 Sep. 8, 2022

(30) Foreign Application Priority Data

Aug. 6, 2019 (WO) .................. PCT/JP2019/030890

(51) Int. Cl.

| | |
|---|---|
| ***A61K 31/437*** | (2006.01) |
| ***A61K 31/4178*** | (2006.01) |
| ***A61K 31/454*** | (2006.01) |
| ***A61K 31/502*** | (2006.01) |
| ***A61K 31/5025*** | (2006.01) |
| ***A61K 31/55*** | (2006.01) |
| ***A61P 35/00*** | (2006.01) |

(52) U.S. Cl.

CPC ........ *A61K 31/437* (2013.01); *A61K 31/4178* (2013.01); *A61K 31/454* (2013.01); *A61K 31/502* (2013.01); *A61K 31/5025* (2013.01); *A61K 31/55* (2013.01); *A61P 35/00* (2018.01)

(58) Field of Classification Search

None

See application file for complete search history.

(56) References Cited

U.S. PATENT DOCUMENTS

| | | | | |
|---|---|---|---|---|
| 12,414,940 | B2 * | 9/2025 | Ohkubo | A61K 31/437 |
| 2012/0108589 | A1 | 5/2012 | Kitade et al. | |
| 2016/0228417 | A1 * | 8/2016 | Muraoka | A61K 31/506 |
| 2020/0281904 | A1 * | 9/2020 | Muraoka | A61K 31/52 |
| 2021/0177813 | A1 * | 6/2021 | Ohkubo | A61K 9/0053 |

FOREIGN PATENT DOCUMENTS

| | | | | |
|---|---|---|---|---|
| EP | 3 053 578 A1 | 8/2016 | | |
| JP | 2006-306775 A | 11/2006 | | |
| KR | 10-2016-0045900 A | 4/2016 | | |
| WO | WO 2011/004610 A1 | 1/2011 | | |
| WO | WO 2015/046498 A1 | 4/2015 | | |
| WO | WO-2019133697 A1 * | 7/2019 | | A61K 39/3955 |

OTHER PUBLICATIONS

Panagiotis Konstantinopoulos et al. "In vivo synergism between PARP-inhibitor olaparib and HSP90-inhibitor AT13387 in high grade serous ovarian cancer patient derived xenografts." Journal of Clinical Oncology 2016, 34, 15, e17045-e17045. DOI:10.1200/JCO.2016.34.15_suppl.e17045 (Year: 2016).*

Suzuki et al. "TAS-116 Second-generation HSP90-a/b inhibitor Cancer Therapy" Drugs of the Future, 2018, 43, 1, 13-21. DOI:10.1358/dof.2018.043.01.2746373. Abstract Only. (Year: 2018).*

Lee et al. "TAS-116, a novel Hsp90 inhibitor, selectively enhances radiosensitivity of human cancer cells to X-rays and carbon ion radiation" Mol Cancer Ther 2017, 16, 1, 16-24. DOI: 10.1158/1535-7163.MCT-16-0573 (Year: 2017).*

Uno et al. "Discovery of 3-Ethyl-4-(3-isopropyl-4-(4-(1-methyl-1H-pyrazol-4-yl)-1H-imidazol-1-yl)-1H-pyrazolo[3,4-b]pyridin-1-yl) benzamide (TAS-116) as a Potent, Selective, and Orally Available HSP90 Inhibitor" J. Med. Chem. 2019, 62, 2, 531-551 DOI: 10.1021/acs.jmedchem.8b01085 Published Dec. 7, 2018 (Year: 2018).*

Reagan-Shaw et. al. "Dose translation from animal to human studies revisited". FASEB J, 2008, 22, 3, 659-661. DOI: 10.1096/fj.07-9574LSF (Year: 2008).*

(Continued)

*Primary Examiner* — Jennifer A Berrios
*Assistant Examiner* — Sophia Reilly
(74) *Attorney, Agent, or Firm* — Oblon, McClelland, Maier & Neustadt, L.L.P.

(57) ABSTRACT

Provided is a novel method for treating cancer with a high antitumor effect. The present invention provides an antitumor agent comprising an azabicyclo compound of the following Formula (I) or a salt thereof and a poly(adenosine 5'-diphosphate-ribose) polymerase inhibitor which are administered in combination.

(I)

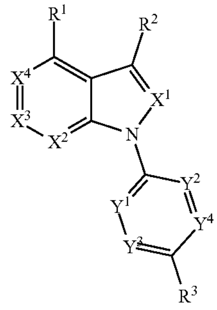

5 Claims, No Drawings

(56) References Cited

OTHER PUBLICATIONS

ClinicalTrials.gov, NCT02965885 A Study of TAS-116 in Patients With Solid Tumors. NIH, https://clinicaltrials.gov/study/NCT02965885?tab=history&a=3#version-content-panel (accessed Oct. 20, 2025). Published Apr. 4, 2018. (Year: 2018).*
International Search Report and Written Opinion issued Sep. 8, 2020 in PCT/JP2020/030017 filed Aug. 5, 2020, 5 pages.
Luke Whitesell, et al., "HSP90 and the chaperoning of cancer," Nature Reviews Cancer, vol. 5, Oct. 2005, pp. 761-772.
Adeela Kamal, et al., "Therapeutic and diagnostic implications of Hsp90 activation," TRENDS in Molecular Medicine, vol. 10, No. 6, Jun. 2004, pp. 283-290.
Udai Banerji, "Heat Shock Protein 90 as a Drug Target: Some Like It Hot," Clin. Cancer Res., vol. 15, No. 1, Jan. 1, 2009, 7 pages.
Tony Taldone, et al., "Targeting Hsp90: small-molecule inhibitors and their clinical development," Current Opinion in Pharmacology, vol. 8, 2008, pp. 370-374.
Yanyan Li, et al., "New developments in Hsp90 inhibitors as anti-cancer therapeutics: Mechanisms, clinical perspective and more potential," Drug Resistance Updates, vol. 12, 2009, pp. 17-27.
David A. Proia, et al., "Synergistic activity of the Hsp90 inhibitor ganetespib with taxanes in non-small cell lung cancer models," Invest New Drugs, vol. 30, 2012, pp. 2201-2209.
Peter C. Fong, M.D., et al., "Inhibition of Poly(ADP-Ribose) Polymerase in Tumors from *BRCA* Mutation Carriers," The New England Journal of Medicine, vol. 361, No. 2, Jul. 9, 2009, pp. 123-134.
Rashid Gabbasov, et al., "Targeted blockade of HSP90 impairs DNA-damage response proteins and increases the sensitivity of ovarian carcinoma cells to PARP inhibition," Cancer Biology & Therapy, vol. 20, No. 7, 2019, pp. 1035-1045.
Panagiotis Konstantinopoulos, et al., "In vivo synergism between PARP-inhibitor olaparib and HSP90-inhibitor AT13387 in high grade serous ovarian cancer patient derived xenografts," Journal of Clinical Oncology, vol. 34, No. 15, 2017, 4 pages.
Rule 132 Declaration submitted to the USPTO on Nov. 27, 2018 in U.S. Appl. No. 15/493,479 (issued as U.S. Pat. No. 10,849,886), a disclosure related to PCT Rule 4.17(v)., 4 pages.
H. Nakajima, et al., "FR1-6: A Phase 1 Study of PARP inhibitor (Niraparib) plus HSP90 Inhibitor (Pimitespib) in Solid Tumors: Dose-escalation Results from the NiraPim (EPOC2102) Study," JSCO 2024 Frontier 1 session, as listed in JSCO2024 Frontier 1 Program PDF (Oct. 24, 2024).
Y. Kawamoto, et al., "A phase 1 study of PARP inhibitor (niraparib) plus HSP90 inhibitor (pimitespib) in solid tumors: Dose-expansion results from the NiraPim (EPOC2102) study," Journal of Clinical Oncology, vol. 43, No. 16 suppl, https://doi.org/10.1200/JCO.2025.43.16_suppl.307 (2025).
Naito et al., "Pimitespib in patients with advanced gastrointestinal stromal tumors in Japan: an expanded access program" International Journal of Clinical Oncology, Feb. 28, 2025, 9 pages. doi: 10.1007/s10147-025-02726-0.
Tsuge et al., "The HSP90 Inhibitor Pimitespib Targets Regulatory T Cells in the Tumor Microenvironment" Cancer Immunology Research, Feb. 3, 2025, vol. 13, No. 2, pp. 273-285. doi: 10.1158/2326-6066.CIR-24-0713.
Doi et al., "Pimitespib for the treatment of advanced gastrointestinal stromal tumors and other tumors" Future Oncology, vol. 20, No. 9, Dec. 5, 2023 (Infographic attached), 15 pages.
Naoki et al., "Cardiovascular safety of pimitespib in patients with advanced solid tumors: An open-label, nonrandomized, phase 1 study" Cancer, vol. 130 No. 21, 2024, pp. 1-12, doi: 10.1002/cncr.35447.
Matsubara et al., "CHAPTER-Platform-201: Phase 2 trial of pimitespib plus enzalutamide for patients with metastatic castration-resistant prostate cancer," Journal of Clinical Oncology, 2025 ASCO Genitourinary Cancers Symposium, vol. 43, No. 5, 2025, 8 pages.
Nakajima et al., "A Phase 1 Study of PARP inhibitor (Niraparib) plus HSP90 inhibitor (Pimitespib) in Solid Tumors: The NiraPim (EPOC2102) Study," Annals of Oncology, ESMO Congress 2024, vol. 35, No. 2, Sep. 14, 2024, 2 pages.
Naito et al., "Treatment Patterns in Patients with Advanced Gastrointestinal Stromal Tumor in Japan: An Administrative Claims Database Study," 22nd Japanese Society of Medical Oncology Annual Meeting, Mar. 7, 2025, 25 pages.
Komatsu et al., "Treatment Patterns in Patients with Advanced Gastrointestinal Stromal Tumor in Japan: An Administrative Claims Database Study," Journal of Clinical Oncology, [Poster Bd J2 and Abstract 811], 2025 ASCO Gastrointestinal Cancers Symposium, vol. 43, No. 5, 2025, 7 pages.
Yong et al., "CHAPTER-GIST-101: A phase I study of pimitespib combined with imatinib in patients with imatinib-refractory gastrointestinal stromal tumor," Annals of Oncology, vol. 35, No. 4, ESMO Asia Congress 2024, Dec. 7, 2024, 2 pages.
Zalcberg, "CHAPTER-GIST-101: A phase I study of pimitespib combined with imatinib in patients with imatinib refractory gastrointestinal stromal tumor," GISTT Summit 2024, Oct. 2024, 1 page.
Hirano et al., "CHAPTER-GIST-101: A phase I study of pimitespib combined with imatinib in patients with imatinib-refractory gastrointestinal stromal tumor," Journal of Clinical Oncology, vol. 42, No. 23, 2024 ASCO Breakthrough, Aug. 8, 2024, (program guide attached), 12 pages.
Nakajima et al., "A Phase 1 Study of PARP Inhibitor (Niraparib) plus HSP90 Inhibitor (Pimitespib) in Solid Tumors: Dose-escalation Results from the NiraPim (EPOC2102) Study," JSCO 62nd Annual Meeting, Oct. 24, 2024 (program attached), 18 pages.
Shimomura et al., "The efficacy and safety of pimitespib in patients with solid tumors: a phase 1 study to assess cardiac safety," JSMO2024, Feb. 22, 2024 (program attached), 18 pages.
Okuhira et al., "Differences in dissolution behavior of after pH-shift basic compounds due to change in API manufacturing process," The 49th Kansai Physical Properties Research Association, Mar. 31, 2024, 79 pages (with unedited computer-generated English Translation).
Ohkubo et al., "TAS-116, a highly selective inhibitor of heat shock protein 90a/i3, inhibits tumor growth in biliary tract cancer mouse models" 26th EORTC-NCI-AACR, Nov. 18, 2014, 1 page.
Ohkubo et al., "A multi-pronged, single-agent approach to treating cancers by targeting the molecular chaperone heat shock protein 90," 73rd JCA, Sep. 25, 2014, 18 pages.
Ohkubo et al., "Discovery of TAS-116: A Novel Inhibitor of HSP90a and HSP9013" 13th Discovery on Target Targeting the Unfolded Protein Response, Sep. 2015, 29 pages.
Saito et al., "The efficacy of novel HSP90 inhibitor, TAS-116, against gastrointestinal stromal tumors" Cancer Science, Abstracts of the 77th Annual Meeting of the Japanese Cancer Association, vol. 109, Issue. S2, Dec. 2018, 1445 pages.
Okubo et al., "Discovery and clinical development of TAS-116, a selective HSP90 inhibitor, for the treatment of advanced gastrointestinal stromal tumors" 15th Cancer TR workshop, Jan. 17, 2020, 50 pages (with unedited computer-generated English translation).
Okubo et al., "for the treatment of advanced gastrointestinal stromal tumors. Creation of HSP90 inhibitor pimitespib," Symposium on Biological Function and Drug Discovery, Aug. 25, 2023, 54 pages (with unedited computer-generated English translation).
Uno et al., "novel oral HSP90 inhibitor," Tohoku University, Jul. 12, 2019, 218 pages (with English Translation).
Uno et al., "Discovery of TAS-116 as a novel orally available HSP90 inhibitor," 37th Medicinal Chemistry Symposium, Nov. 27, 2019, 3 pages.
Uno et al., "Creation of TAS-116, a novel oral HSP90 inhibitor," The 141st Pharmaceutical Society of Japan, Mar. 27, 2021, 54 pages (with unedited computer-generated English machine translation).
Ohkubo et al., "Discovery and clinical development of TAS-116, a selective HSP90 inhibitor, for the treatment of advanced gastrointestinal stromal tumors," 15th JAMTTC TR workshop, Jan. 17, 2020, 77 pages (with unedited computer-generated English machine translation).
Ikebe et al., "A highly selective HSP90a/i3 inhibitor, TAS-116, demonstrates its potent growth suppressive activity to adult T-cell

(56) References Cited

OTHER PUBLICATIONS leukemia in preclinical models," The 18th International Human Retrovirus HTLV Conference, Oita University, Mar. 2017, 2 pages.
Uno et al., "Creation of a Novel HSP90 Inhibitor, TAS-116" Kitasato University, Nov. 9, 2021, 150 pages (with unedited computer-generated English machine translation).
Kodama et al., "a novel oral HSP90 inhibitor, TAS-116" Manuscript_2013 Molecular Target Therapy of Cancer, Sep. 10, 2013, 4 pages (with unedited computer-generated English machine translation).
Doi et al., "Pimitespib pooled safety profile analysis in patients with solid tumors, including gastrointestinal stromal tumor," FR1-1, JSCO2023, The 61st Annual Meeting of the Japan Society of Clinical Oncology, Oct. 19, 2023, 13 pages.
Komatsu et al., "An open-label, crossover study to compare different formulations and evaluate effect of food on pharmacokinetics of pimitespib in patients with advanced solid tumors," Investigational New Drugs, Aug. 6, 2022, vol. 40, pp. 1011-1020.
Kurokawa et al., "Pimitespib, an oral inhibitor of heat shock protein 90 in advanced gastrointestinal stromal tumor refractory to standard therapy: Results from the expanded access program," FR1-7, JSCO2023, The 61st Annual Meeting of the Japan Society of Clinical Oncology, Oct. 19, 2023, 19 pages.
Kasahara et al., "A Phase 1 Study to Compare Formulations and Evaluate the Effect of Food on Pimitespib in Patients with Solid Tumors," JSMO2022, Feb. 18, 2022, 12 pages.
Sawaki et al., "A phase III trial of pimitespib (TAS-116) in patients with advanced gastrointestinal stromal tumor: CHAPTER-GIST-301," 2022 The Japanese Society of Medical Oncology Annual Meeting PS4-3 JSMO2022, Feb. 19, 2022, 31 pages.
Hirano et al., "CHAPTER-GIST-101: A phase I study of pimitespib combined with imatinib in patients with imatinib-refractory gastro-intestinal stromal tumor," Gastrointestinal Cancer, TPS97, ASCO Journal of Clinical Oncology, vol. 42, No. 23_Supplement, 1 page.
Ikebe et al., "TAS-116 pimitespib a heat shock protein 90 inhibitor shows efficacy in preclinical models of adult T-cell leukemia," Cancer Science, 2022, vol. 113, pp. 684-696.
Shimizu et al., "PBPK Modeling Using Simcyp to Evaluate Drug-Drug Interaction Potential of Pimitespib," Otsuka Simcyp User Forum, Dec. 15, 2022, 35 pages.
Uno et al., "Abstract C127: TAS-116, an orally available HSP90αβ selective inhibitor-Synthesis and biological evaluation," Mol Cancer Ther, vol. 12, No. 11_Supplement, AACR-NCI-EORTC, Nov. 1, 2013, 6 pages.
Muraoka et al., "TAS-116, an orally available HSP90α/β selective inhibitor, has potent antitumor activity in small cell lung cancer as a single agent and in combination with an anthracycline derivative, amrubicin," Mol Cancer Ther, vol. 12, No. 11_Supplement, Nov. 2013, AACR-NCI-EORTC, 6 pages.
Muraoka et al., "TAS-116, an orally available HSP90α and β selective inhibitor, exhibits synergistic effects in combination with taxanes in EGFR-tyrosine kinase inhibitor-resistant human NSCLC xenograft models through the downregulation of key molecules involved in drug resistance of cancer chemotherapy," C129, vol. 12, No. 11_Supplement, Nov. 1, 2013, AACR-NCI-EORTC, 5 pages.
Yoshimura et al., "Thermodynamic Dissection of Potency and Selectivity of Cytosolic Hsp90 Inhibitors," J. Med. Chem., vol. 64, 2021, pp. 2669-2677, 9 pages.
Uno et al, "Discovery of TAS-116, a novel oral HSP 90 inhibitor," 37th Symposium on Medicinal Chemistry, Medchem News, vol. 30, No. 3, 2020, pp. 133-136, 2020, 12 pages (with unedited computer-generated English translation).
Okihira et al., "Basic Compounds in Cancer Patients In vitro study about the absorption of weakly basic drugs in cancer patients," The 38th Annual Meeting of the Pharmaceutical Society of Japan [2-6] Absorption and distribution5 2-6-11, May 17, 2023, 56 pages (with unedited computer-generated English translation).
Uno et al., "Discovery of a Novel Oral HSP90 Inhibitor, Pimitespib (TAS-116)," The 33rd New Drug Discussion Meeting, Sep. 5, 2023, [slides and agenda], 78 pages (with unedited computer-generated English machine translation).
Kawazoe et al., "TAS-116, an Oral HSP90 Inhibitor, in combination with nivolumab in patients with colorectal cancer and other solid tumors: an open-label, dose-finding, and expansion phase 1b trial (EPOC1704)", Journal of Clinical Oncology, 2020 ASCO Annual Meeting, vol. 38, No. 15, May 25, 2020, 4 pages.
Chong, K.T et al., Crystal structure of Hsp90-alpha N-terminal domain in complex with 2-(4-Hydroxy-cyclohexylamino)-4-[5-(4-phenyl-imidazol-1-yl)-isoquinolin-1-yl]-benzamide FullwwPDB X-ray Structure Validation Report_3wq9_RCSB PDB, Jan. 23, 2014, 14 pages.
Yoshimura et al., "Accelerating Drug Discovery with Thermodynamics," Life Science Day 2013 Lecture(1), Jul. 3, 2013, 50 pages (with unedited computer-generated English translation).
Uno et al., "Discovery of TAS-116, a novel oral HSP 90 inhibitor," 37th Symposium on Medicinal Chemistry lecture summary, Sep. 27, 2019, 2 pages (with unedited computer-generated English translation).
Suzuki et al., "Antitumor activities of an oral selective HSP90a/b inhibitor, TAS-116, in combination with bortezomib in multiple myeloma," Leukemia, vol. 29, No. 2, Feb. 2015, 9 pages. doi:10.1038/leu.2014.300.
Ohkubo et al., "Drug Discovery of HSP90 Inhibitor pimitespib and Approach to Resistant Cancer," The 1st Tokyo University of Science Symposium on Integrative Research of Cancer, Immunology and Mathematics, Dec. 2, 2023, 59 pages (with unedited computer-generated English translation).
Takahashi et al., "Final analysis of phase III trial of pimitespib (TAS-116) in patients with advanced GIST: CHAPTER GIST 301," O14-4 JSMO2023, Mar. 18, 2023, 18 pages.
Shimomura et al., "The efficacy and safety of pimitespib in patients with solid tumors: A phase 1 study to assess cardiac safety," JSMO2024, (program attached), Feb. 22, 2024, 19 pages.
Karayama et al., "Cardiovascular Safety of Pimitespib in Patients with Solid Tumors: A Phase 1 Study" JSMO2023, (program attached), Mar. 16, 2023, 13 pages.
Suzuki et al., "Anti-tumor activities of selective HSP90α/β inhibitor, TAS-116, in combination with bortezomib in multiple myelomaleukemia," Leukemia, Feb. 2015, vol. 29, No. 2, 30 pages.
Suzuki et al., "Combination treatment of HSP90 α / β inhibitor and RAS-RAF-MEK-ERK inhibitor for myeloma treatment," International Journal of Myeloma, vol. 5, No. 2, 2015, 8 pages.
Suzuki et al., "Combination of a Selective HSP90α/β Inhibitor and a RAS-RAF-MEK-ERK Signaling Pathway Inhibitor Triggers Synergistic Cytotoxicity in Multiple Myeloma Cells," PLoS One, Dec. 2, 2015, vol. 10, No. 12, 20 pages.
Shimomura et al., "Abstract: B87: First in-human Phase I dose-escalation study of TAS-116, a novel, orally active HSP90 α/β selective inhibitor, in patients with advanced solid tumors," Mol Cancer Ther, 2015, vol. 14, No. 12_Supplement 2, AACR-NCI-EORTC 2015_#B87, 3 pages.
Ohkubo et al., "The discovery and development of oral HSP90α/β inhibitor, TAS-116," Molecular Chaperones in Cancer, session#5 P.65 (program attached), May 4, 2017, 166 pages.
Saito et al., "TAS-116 inhibits oncogenic KIT signalling on the Golgi in both imatinib-naïve and imatinib-resistant gastrointestinal stromal tumours," Br J Cancer. Mar. 2020, vol. 122, No. 5, pp. 658-667.
Jackson et al., "Pharmacologic dissection of the overlapping impact of heat shock protein family members on platelet function," J Thromb Haemost, May 2020, vol. 18, No. 5, pp. 1197-1209.
Kihara et al., "Pimitespib is effective on cecal GIST in a mouse model of familial GISTs with KIT-Asp820Tyr mutation through KIT signaling inhibition," Experimental and Molecular Pathology, vol. 123, 2021, 04692, 8 pages.
Teranishi et al., "Combination of pimitespib (TAS-116) with sunitinib is an effective therapy for imatinib-resistant gastrointestinal stromal tumors," Int J Cancer, Jun. 15, 2023, vol. 152, No. 12, pp. 2580-2593, 14 pages.
Sano et al., "Characterization of cell line with dedifferentiated GIST-like features established from cecal GIST of familial GIST model mice," Pathol Int., May 2023, vol. 73, No. 5, pp. 181-187.

(56) References Cited

OTHER PUBLICATIONS

Naito et al., "CHAPTER-GIST-101: A phase I study of pimitespib combined with imatinib in patients with imatinib-refractory gastrointestinal stromal tumor," 1917MO S1031_vol.34_Issue S2_ESMO, 2023, 12 pages.
Naito et al., "Current status of and future prospects for the treatment of unresectable or metastatic gastrointestinal stromal tumours," Gastric Cancer, May 2023, vol. 26, No. 3, pp. 339-351.
Doi et al., "Pimitespib for the treatment of advanced gastrointestinal stromal tumors and other tumors," Future Oncol., Mar. 2024, vol. 20, No. 9, 13 pages.
Shibata et al. "Utility of Cryopreserved Hepatocytes Suspended in Serum to Predict Hepatic Clearance in Dogs and Monkeys," Drug Metab Pharmacokinet, 2014, vol. 29, No. 2, pp. 168-176.
Kawazoe et al.,"TAS-116 (Pimitespib), an Oral HSP90 Inhibitor, in Combination with Nivolumab in Patients with Colorectal Cancer and Other Solid Tumors: An Open-Label, Dose-Finding, and Expansion Phase Ib Trial (EPOC1704)," Clin Cancer Res., Dec. 15, 2021, vol. 27, No. 24, pp. 6709-6715.
Takei et al.,"Multiomic molecular characterization of the response to combination immunotherapy in MSS/pMMR metastatic colorectal cancer," J Immunother Cancer., Feb. 8, 2024, vol. 12, No. 2, e008210, 21 pages.
"A phase 2 study of TAS-116 in patients with GIST" Mar. 3, 2016; Trial ID CT2080223127; JapicCTI-163182 URL: https://jrct.niph.go.jp/pages/en-detail/54738/RCT/3, 3 pages.
Hitotsumachi et al., "TAS-116, an Orally Highly Potent HSP90 α/β Selective Inhibitor, Leads Minimized Ocular Toxicity in Both Albino and Pigmented Rats," Society of Toxicology Annual Meeting, 2013, 2 pages.
Hitotsumachi et al., "Heat shock protein 90 inhibitor, TAS-116, demonstrates favorable tissue distribution'profiles and leads to minimized ocular toxicity"; European Societies of Toxicology, EUROTOX, 2013, 2 pages.
Kodama et al., "Discovery of a Novel Oral HSP90 Inhibitor, TAS-116-Antitumor Effects Due to High Tumor Translocation and Avoidance of Ocular Toxicity," Japanese Association for Molecular Target Therapy of Cancer, 2013, 3 pages (with unedited computer-generated English translation).
Yoshimura et al., Evolution of highly selective HSP90 α/β inhibitors with unique binding mode, 24th EORTC—NCI—AACR Symposium on Molecular Targets and Cancer Therapeutics, 2012, 1 page.
Kodama et al., "TAS-116, a novel, orally bioavailable highly potent HSP90α/β selective inhibitor demonstrates favorable tissue distribution properties which lead to minimized ocular toxicity," 24th EORTC—NCI—AACR Symposium on Molecular Targets and Cancer Therapeutics, 2012, 1 page.
Ohkubo et al., TAS-116, a novel, orally bioavailable HSP90α/β selective inhibitor demonstrates highly potent antitumor activity in preclinical models with a favorable PK profile, 24th EORTC—NCI—AACR Symposium on Molecular Targets and Cancer Therapeutics, 2012, 1 page.
Ohkubo et al., "TAS-116, a Highly Selective Inhibitor of Heat Shock Protein 90a and J3, Demonstrates Potent Antitumor Activity and Minimal Ocular Toxicity in Preclinical Models", Molecular Cancer Therapeutics, 2015, vol. 14, No. 1, 15 pages.
Renouf et al., "Ocular Toxicity of Targeted Therapies", Journal of Clinical Oncology, 2012, vol. 30, No. 26, pp. 3277-3286.
Suzuki et al., "TAS-116 Second-generation HSP90-a/J3 inhibitor Cancer therapy", Drugs of the Future, 2018, vol. 43, No. 1, 11 pages.
JapicCTI-163182, JAPIC Clinical Trials Information, Japan Pharmaceutical Information Center, Retrieved from the Internet: [URL:http://www.clinicaltrials.jp/user/cteSearch.jsp], 2017, Retrieved on Jul. 18, 2018, 6 pages.
Yanagitani et al., "First-in-human phase I study of an oral HSP90 inhibitor, TAS-116, in advanced solid tumors," ASCO Meeting Library, Retrieved from the Internet: [URL:https://meetinglibrary.asco.org/record/149483/abstract], Presented Jun. 5, 2017, Retrieved on Jul. 10, 2018, 3 pages.
Kurokawa et al., "Phase II study of TAS-116, an oral inhibitor of heat shock protein 90 (HSP90), in metastatic or unresectable gastrointestinal stromal tumor refractory to imantinib, sunitinib and regorafenib", Annals of Oncology, Clinical trial JapicCTI-163182, vol. 28, Suppl. 5, 2017, 4 pages.
Shimomura et al., "Abstract B87: First-in-human Phase I dose escalation study of TAS-116, a novel, orally active HSP90α and HSP90β selective inhibitor, in patients with advanced solid tumors", Annals of Oncology, Proceedings of the AACR-NCI-EORTC International Conference: Molecular Targets and Cancer Therapeutics; 2015, vol. 14, Issue 12, Suppl. 2, 5 pages.
Taiho Oncology, Inc., "History of Changes for Study: NCT02965885 A Study of TAS-116 in Patients With Solid Tumors," Archive history for NCT02965885, ClinicalTrials.gov archive, U.S. National Library of Medicine, Retrieved from the Internet: [URL: https://clinicaltrials.gov/ct2/history/NCT02965885?A=1&B=1&C=merged], 2016, Retrieved on Jul. 10, 2018, 6 pages.
Yong et al., "Phase I study of KW-2478, a novel Hsp90 inhibitor, in patients with B-cell malignancies", British Journal of Cancer, vol. 114, 2016, pp. 7-13.
"ESMO Congress", ESMO 2017 In partnership with European Association for Cancer Research (EACR), Sep. 11, 2017, 326 pages.
Kurokawa et al,"Pimitespib for advanced gastrointestinal stromal tumor: a plain language summary of the CHAPTER-GIST-301 study" Future Oncology Accepted for publication: Jun. 23, 2025, 13 pages.
Muraoka et al., "Pimitespib, an HSP90 Inhibitor, Enhances the Efficacy of PARP Inhibitors in PARP Inhibitor-Insensitive Breast Cancer Cells" Cancer Science, 2025: 0:1-13, https://doi.org/10.1111/cas.70058 Accepted: Mar. 10, 2025, 13 pages.
Muraoka et al., "Pimitespib (TAS-116), an HSP90 inhibitor, overcomes resistance to androgen receptor pathway inhibitors in prostate cancer by simultaneously targeting several key resistance mechanisms" ASCO AACR Annual meeting 2025_Cancer Res (2025) 85 (8_Supplement_1): 4437 [abstract] https://doi.org/10/1158/1538-7445.AM2025-4437_ Apr. 21, 2025, 5 pages.
Muraoka et al.,"Pimitespib (TAS-116), an HSP90 inhibitor, overcomes resistance to androgen receptor pathway inhibitors in prostate cancer by simultaneously targeting several key resistance mechanisms" ASCO AACR Annual meeting 2025_Cancer Res (2025) 85 (8_Supplement_1):4437 [poster] https://doi.org/10.1158/1538-7445.AM2025-4437_ Apr. 21, 2025, 1 page.
Kawamoto et al., "A phase 1 study of PARP Inhibitor (niraparib) plus HSP90 inhibitor (pimitespib) in solid tumors: Dose-expansion results from the NiraPim (EPOC2102) study." [poster] ASCO Annual Meeting_Journal of Clinical Oncology vol. 43, No. 16_suppl_ https://doi.org/10.1200/JCO.2025.43.16_suppl.3079_May 26, 2025. 3 pages.
T. Uno et al.,"Development of a Novel Oral HSP90 Inhibitor"—"TAS-116 (Pimitespib)", Lecture slides held at the Graduate School of Hokkaido University, Dec. 2, 2025 in Japanese (71 pages) with English supplementary summary (1 page); total 72 pages.
Y. Kurokawa et al.,"CHAPTER-GIST-101. A phase I trial of pimitespio and imatinib in patients with gastrointestinal stromal tumors refractory to imatinib"; 266eTiP, abstract_ESMO Rare Cancers_vol. 5, Issue S, pp. 60-81, Supplement, Mar. 1, 2026.100472 (2 pages).
Y. Kurokawa et. al.,"CHAPTER-GIST-101; A phase I trial of pimitespib and imatinib in patients with gastrointestinal stromal tumors refractory to imatinib"; 266eTiP_NCT05245968_POSTER_ESMO Rare Cancers, Mar. 13, 2026, 100472 (1 page).
Y. Miyata et al., "The therapeutic target Hsp90 and cancer hallmarks"; Current Pharmaceutical Design, vol. 19, Issue 3, 2013, 347-365.
T. Ratajczak et al., "Hsp90 as a therapeutic target in endocrinology: current evidence," Research and Reports in Endocrine Disorders, vol. 5, 2015, pp. 141-155.
A. Röhl et al., "The chaperone Hsp90: changing partners for demanding clients", Trends in Biochemical Sciences, vol. 38, 2013, 253-262, DOI: 10.1016/j.tibs.2013.02.003.

(56) References Cited

OTHER PUBLICATIONS

M. A. Bismonte et al., "Heat Shock Protein 90: Inhibitors and Chemical Biology," Journal of Medicinal Chemistry, 53, 2010, pp. 3-17.
L. Wright et al., "Structure-Activity Relationships in Purine-Based Inhibitor Binding to HSP90 Isoforms," Chemistry & Biology, 11, 2004, pp. 775-785.
Kurokawa et al. "Pooled safety analysis of pimitespib for the treatment of patients with advanced gastrointestinal stromal tumors", International Journal of Clinical Oncology: Nov. 20, 2025, DOI: 10.1007/s10147-025-02917-9.
Komatsu et al. "Quality of Life Outcomes with Pimitespib in Patients with Advanced Gastrointestinal Stromal Tumor: Results From the Randomized, Double-blind, Placebo-controlled, Phase 3, Chapter-GIST-301 Study", ESMO Open: Mar. 5, 2026, vol. 11, p. 1-9, DOI: 10.1016/j.esmoop.2026.106088.

* cited by examiner

COMBINATION THERAPY FOR CANCER USING AZABICYCLIC COMPOUND AND POLY(ADENOSINE 5'-DIPHOSPHATE-RIBOSE) POLYMERASE INHIBITOR

CROSS-REFERENCE TO RELATED APPLICATIONS

The present application is a 35 U.S.C. § 371 national stage patent application of International patent application PCT/JP2020/030017, filed on Aug. 5, 2020, which is based on and claims the benefits of priority to International patent application PCT/JP2019/030980, filed on Aug. 6, 2019. The entire contents of these applications are incorporated herein by reference.

CROSS-REFERENCE TO RELATED APPLICATIONS

The present application claims the priority based on the specification of PCT Application No. PCT/JP2019/030980 (the disclosure of which is incorporated herein by reference in its entirety) filed on Aug. 6, 2019.

FIELD OF THE INVENTION

The present invention relates to an antitumor agent containing an azabicyclo compound or a salt thereof and a poly(adenosine 5'-diphosphate-ribose) polymerase inhibitor (hereinafter, also referred to as a "PARP inhibitor") in combination, a treatment method related to the combination, etc.

BACKGROUND OF THE INVENTION

A group of proteins called molecular chaperons promotes the formation of the functional structures of other proteins or maintains these structures, promotes correct association, inhibits unnecessary aggregation, protects other proteins from degradation, and promotes secretion (Non-Patent Literature 1). HSP90 is a molecular chaperone as abundant as approximately 1 to 2% of all intracellular soluble proteins and is unnecessary for biosynthesis of the majority of polypeptides, unlike other chaperon proteins (Non-Patent Literature 1). Signaling-related factors (for example, ERBB1/EGFR, ERBB2/HER2, MET, IGF1R, KDR/VEGFR, FLT3, ZAP70, KIT, CHUK/IKK, BRAF, RAF1, SRC, and AKT), cell cycle regulatory factors (for example, CDK4, CDK6, Cyclin D, PLK1, and BIRC5), and transcriptional regulators (for example, HIF-1α, p53, androgen receptor, estrogen receptor, and progesterone receptor) are known as main client proteins whose structural formation or stability is controlled through interaction with HSP90 (Non-Patent Literatures 2 and 3). HSP90 is deeply involved in cell proliferation or survival by maintaining the normal functions of these proteins. Further, HSP90 is required for the normal functions of mutated or chimeric factors (for example, BCR-ABL and NPM-ALK) which cause carcinogenesis or exacerbation of cancer. This indicates the importance of HSP90 particularly for processes such as carcinogenesis, cancer survival, growth, exacerbation, and metastasis (Non-Patent Literature 2).

The inhibition of the chaperon functions of HSP90 by specific inhibitors such as geldanamycin causes the inactivation, destabilization, and degradation of the client proteins, resulting in induction of a halt in cell proliferation or apoptosis (Non-Patent Literature 4). In terms of the physiological functions of HSP90, HSP90 inhibitors are characterized in that they can simultaneously inhibit multiple signaling pathways involved in cancer survival and growth. Thus, the HSP90 inhibitors can serve as pharmaceuticals having extensive and effective anticancer activity. Moreover, from the findings that cancer cell-derived HSP90 has higher activity and higher affinity for ATP or inhibitors than those of normal cell-derived HSP90, it has been expected that the HSP90 inhibitors would serve as pharmaceuticals having high cancer selectivity (Non-Patent Literature 5).

A plurality of HSP90 inhibitors are currently under clinical development as anticancer agents. Ganetespib, which is most advanced, is being developed as a single agent, and in addition, its combination trial with another antitumor agent such as docetaxel is also being carried out (Non-Patent Literature 6).

A new type of HSP90 inhibitor has also been reported (Patent Literature 1). There is a demand for HSP90 inhibitors having a higher antitumor effect and fewer side effects.

PARP recognizes the end of a single-strand break that has occurred in nuclear DNA, and binds to the DNA. The PARP bound with the nuclear DNA is activated so as to add ADP-ribose to the PARP itself or DNA repair-related proteins with $NAD^+$ as a substrate, causing poly-ADP-ribosylation. Usually, the poly-ADP-ribosylation activates DNA repair reaction, whereas excessive activation of PARP induces the depletion of $NAD^+$ and ATP and further, the cleavage of apoptosis-inducing factor (AIF) localized in mitochondria. AIF released into the cytoplasm by cleavage is translocated, together with endonuclease G localized in mitochondria, to the nucleus where the fragmentation of nuclear DNA is caused to induce cell death.

PARP repairs single-strand DNA breaks, while BRCA1 and BRCA2 play an important role in double-strand DNA repair by homologous recombination. When PARP is inhibited in cells deficient in homologous recombination without functions of BRCA1 and BRCA2 genes, DNA damage is no longer repaired so that cell death called synthetic lethality is induced. It has previously been reported that BRCA1-deficient cells and BRCA2-deficient cells exhibit a very high tumor growth inhibitory effect by the inhibition of PARP as compared with wild-type cells (Non-Patent Literature 7). In such a way, cancer treatment is ongoing by using molecular targeting drugs selectively inhibiting PARP. In recent years, a PARP inhibitor olaparib has been approved as an anticancer agent.

It has been further reported that the block of HSP90 as a target promotes the inactivation and degradation of proteins necessary for DNA damage repair (DDR) and elevates the sensitivity of ovarian cancer cells to PARP inhibitors (Non-Patent Literature 8).

However, there currently exists no established method for treating cancers in relation to use of an HSP90 inhibitor and a PARP inhibitor in combination.

CITATION LIST

Patent Literature

Patent Literature 1: WO 2011/004610 A

Non-Patent Literature

Non-Patent Literature 1: Nature Reviews Cancer, 5, 761-772 (2005)

Non-Patent Literature 2: TRENDS in Molecular Medicine 6, 283-290 (2004)
Non-Patent Literature 3: Clin Can Res 15, 9-14 (2009)
Non-Patent Literature 4: Current Opinion in Pharmacology, 8, 370-374 (2008)
Non-Patent Literature 5: Drug Resistance Updates, 12, 17-27 (2009)
Non-Patent Literature 6: Invest New Drugs. 30(6): 2201-9 (2012)
Non-Patent Literature 7: N Engl J Med 361(2): 123-134 (2009)
Non-Patent Literature 8: Cancer Biol Ther 20(7): 1035-1045 (2019)

SUMMARY OF THE INVENTION

Problems to be Solved by the Invention

An object of the present invention is to provide a novel method for treating cancers with a high antitumor effect.

Means for Solving the Problem

The present inventor has conducted diligent studies for attaining the object, and resultantly found that a combination of an azabicyclo compound of Formula (I) given below and a PARP inhibitor markedly potentiates an antitumor effect.

That is, the present invention provides the following inventions [1] to [18].

[1] An antitumor agent comprising an azabicyclo compound of the following Formula (I) or a salt thereof and a PARP inhibitor which are administered in combination:

(I)

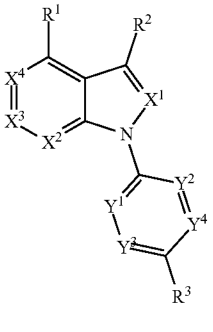

in the formula, $X^1$ represents CH or N;

any one of $X^2$, $X^3$, and $X^4$ is N, and the others represent CH;

any one or two of $Y^4$, $Y^2$, $Y^3$, and $Y^4$ are C—$R^4$, and the others are the same or different and represent CH or N;

$R^1$ represents an optionally substituted mono- or bi-cyclic unsaturated heterocyclic group having 1 to 4 heteroatoms selected from the group consisting of N, S, and O;

$R^2$ represents a hydrogen atom, an optionally substituted alkyl group having 1 to 6 carbon atoms, or an optionally substituted alkenyl group having 2 to 6 carbon atoms;

$R^3$ represents a cyano group or —CO—$R^5$;

$R^4$(s) are the same or different and represent a hydrogen atom, a halogen atom, a cyano group, an optionally substituted alkyl group having 1 to 6 carbon atoms, an alkenyl group having 2 to 6 carbon atoms, an alkoxy group having 1 to 6 carbon atoms, an aromatic hydrocarbon group, —N($R^6$)($R^7$), —S—$R^8$, or —CO—$R^9$;

$R^5$ represents an amino group optionally having a hydroxyl group or an optionally substituted mono- or di-alkylamino group;

$R^6$ and $R^7$ are the same or different and represent a hydrogen atom, an optionally substituted alkyl group having 1 to 6 carbon atoms, a halogenoalkyl group having 1 to 6 carbon atoms, an optionally substituted cycloalkyl group having 3 to 7 carbon atoms, an optionally substituted aralkyl group, an optionally substituted aromatic hydrocarbon group, an optionally substituted saturated heterocyclic group, or an optionally substituted unsaturated heterocyclic group, or $R^6$ and $R^7$ optionally form a saturated heterocyclic group together with a nitrogen atom to which they are bonded;

$R^8$ represents an optionally substituted cycloalkyl group having 3 to 7 carbon atoms or an optionally substituted aromatic hydrocarbon group; and $R^9$ represents a hydrogen atom, a hydroxyl group, an amino group optionally having a hydroxyl group, or an optionally substituted mono- or di-alkylamino group.

[2] The antitumor agent according to [1], wherein the azabicyclo compound is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide.

[3] The antitumor agent according to [1] or [2], wherein the PARP inhibitor is one or more selected from the group consisting of olaparib, rucaparib, talazoparib, niraparib, and veliparib.

[4] The antitumor agent according to any of [1] to [3], wherein the azabicyclo compound or the salt thereof and the PARP inhibitor are administered concurrently or separately in a staggered manner to a cancer patient.

[5] An antitumor effect potentiator for a PARP inhibitor, comprising an azabicyclo compound or a salt thereof as an active ingredient, wherein the azabicyclo compound is a compound of the following Formula (I)

(I)

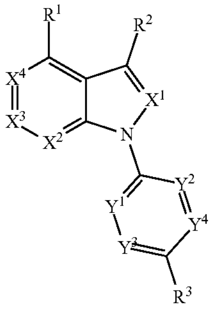

in the formula, $X^1$ to $X^4$, $Y^1$ to $Y^4$, and $R^1$ to $R^9$ are as defined above.

[6] The antitumor effect potentiator according to [5], wherein the azabicyclo compound is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide.

[7] The antitumor effect potentiator according to [5] or [6], wherein the PARP inhibitor is one or more selected from the group consisting of olaparib, rucaparib, talazoparib, niraparib, and veliparib.

[8] The antitumor effect potentiator according to any of [5] to [7], wherein the azabicyclo compound or the salt thereof and the PARP inhibitor are administered concurrently or separately in a staggered manner to a cancer patient.

[9] An antitumor agent comprising an azabicyclo compound or a salt thereof and a PARP inhibitor in combination, wherein the azabicyclo compound is an azabicyclo compound of the following Formula (I):

(I)

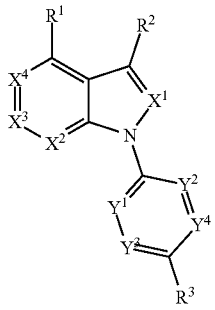

in the formula, $X^1$ to $X^4$, $Y^1$ to $Y^4$, and $R^1$ to $R^9$ are as defined above.

[10] The antitumor agent according to [9], wherein the azabicyclo compound is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide.

[11] The antitumor agent according to [9] or [10], wherein the PARP inhibitor is one or more selected from the group consisting of olaparib, rucaparib, talazoparib, niraparib, and veliparib.

[12] A method for preventing and/or treating tumors, the method comprising the step of administering to a patient prophylactically and/or therapeutically effective amounts of an azabicyclo compound or a salt thereof and a PARP inhibitor, wherein the azabicyclo compound is an azabicyclo compound of the following Formula (I):

(I)

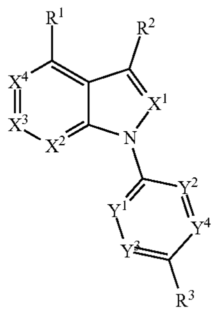

in the formula, $X^1$ to $X^4$, $Y^1$ to $Y^4$, and $R^1$ to $R^9$ are as defined above.

[13] The method for preventing and/or treating tumors according to [12], wherein the azabicyclo compound is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide.

[14] The method for preventing and/or treating tumors according to [12] or [13], wherein the PARP inhibitor is one or more selected from the group consisting of olaparib, rucaparib, talazoparib, niraparib, and veliparib.

[15] The method for preventing and/or treating tumors according to any of [12] to [14], wherein the azabicyclo compound or the salt thereof and the PARP inhibitor are administered concurrently or separately in a staggered manner to a cancer patient.

[16] An antitumor agent for use in the treatment of tumors by administration in combination with a PARP inhibitor, comprising an azabicyclo compound of the following Formula (I) or a salt thereof:

(I)

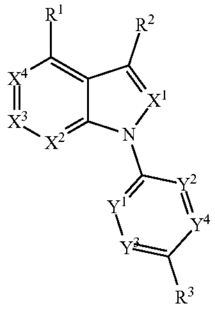

in the formula, $X^1$ to $X^4$, $Y^1$ to $Y^4$, and $R^1$ to $R^9$ are as defined above.

[17] The antitumor agent according to [16], wherein the azabicyclo compound is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide.

[18] The antitumor agent according to [16] or [17], wherein the PARP inhibitor is one or more selected from the group consisting of olaparib, rucaparib, talazoparib, niraparib, and veliparib.

The invention also relates to the following aspects.

A pharmaceutical composition for preventing and/or treating tumors, comprising an azabicyclo compound of Formula (I) or a salt thereof and a PARP inhibitor.

An azabicyclo compound of Formula (I) or a salt thereof for potentiating an antitumor effect of a PARP inhibitor.

Use of an azabicyclo compound of Formula (I) or a salt thereof for potentiating an antitumor effect of a PARP inhibitor.

Use of an azabicyclo compound of Formula (I) or a salt thereof for producing an antitumor effect potentiator for a PARP inhibitor.

An antitumor agent for treating a cancer patient given a PARP inhibitor, comprising an azabicyclo compound of Formula (I) or a salt thereof.

An azabicyclo compound of Formula (I) or a salt thereof for use in antitumor effect potentiation for a PARP inhibitor.

An azabicyclo compound of Formula (I) or a salt thereof for use in the treatment of a tumor in a cancer patient given a PARP inhibitor.

A combination of an azabicyclo compound of Formula (I) or a salt thereof and a PARP inhibitor for use in the treatment of tumors.

A kit product comprising an azabicyclo compound of Formula (I) or a salt thereof and a PARP inhibitor as a combination formulation for concurrent use, sequential use, or use in a staggered manner in preventing and/or treating tumors.

Effects of the Invention

The antitumor agent of the present invention is capable of performing cancer treatment which exerts a high antitumor effect (particularly, a cytoreductive effect, a tumor growth delaying effect (life extending effect), etc.) while suppressing the development of a side effect, and accordingly brings about the long-term survival of cancer patients.

DETAILED DESCRIPTION OF THE INVENTION

The present invention relates to an antitumor agent comprising an azabicyclo compound of Formula (I) or a salt thereof and a PARP inhibitor which are administered in combination, an antitumor effect potentiator, a kit formulation and use of these agents, a method for treating tumors, and a method for potentiating an antitumor effect.

In the present invention, the HSP90 inhibitor which brings about excellent synergistic action with a PARP inhibitor is an azabicyclo compound of the following Formula (I) or a salt thereof:

(I)

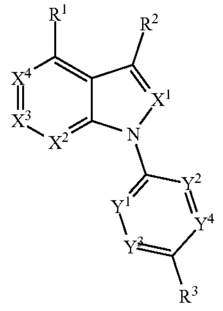

in the formula, $X^1$ represents CH or N;

any one of $X^2$, $X^3$, and $X^4$ is N, and the others represent CH;

any one or two of $Y^1$, $Y^2$, $Y^3$, and $Y^4$ are C—$R^4$, and the others are the same or different and represent CH or N;

$R^1$ represents an optionally substituted mono- or bi-cyclic unsaturated heterocyclic group having 1 to 4 heteroatoms selected from the group consisting of N, S, and O;

$R^2$ represents a hydrogen atom, an optionally substituted alkyl group having 1 to 6 carbon atoms, or an optionally substituted alkenyl group having 2 to 6 carbon atoms;

$R^3$ represents a cyano group or —CO—$R^5$;

$R^4$(s) are the same or different and represent a hydrogen atom, a halogen atom, a cyano group, an optionally substituted alkyl group having 1 to 6 carbon atoms, an alkenyl group having 2 to 6 carbon atoms, an alkoxy group having 1 to 6 carbon atoms, an aromatic hydrocarbon group, —N($R^6$)($R^7$), —S—$R^8$, or —CO—$R^9$;

$R^5$ represents an amino group optionally having a hydroxyl group or an optionally substituted mono- or di-alkylamino group;

$R^6$ and $R^7$ are the same or different and represent a hydrogen atom, an optionally substituted alkyl group having 1 to 6 carbon atoms, a halogenoalkyl group having 1 to 6 carbon atoms, an optionally substituted cycloalkyl group having 3 to 7 carbon atoms, an optionally substituted aralkyl group, an optionally substituted aromatic hydrocarbon group, an optionally substituted saturated heterocyclic group, or an optionally substituted unsaturated heterocyclic group, or $R^6$ and $R^7$ optionally form a saturated heterocyclic group together with a nitrogen atom to which they are bonded;

$R^8$ represents an optionally substituted cycloalkyl group having 3 to 7 carbon atoms or an optionally substituted aromatic hydrocarbon group; and $R^9$ represents a hydrogen atom, a hydroxyl group, an amino group optionally having a hydroxyl group, or an optionally substituted mono- or di-alkylamino group.

In the present specification, examples of the "substituent(s)" include a halogen atom, a hydroxyl group, a cyano group, a nitro group, an alkyl group, a halogenoalkyl group, a cycloalkyl group, a cycloalkyl-alkyl group, an aralkyl group, a hydroxyalkyl group, an alkenyl group, an alkynyl group, an alkoxy group, a halogenoalkoxy group, an alkoxy-alkyl group, a cycloalkoxy group, a cycloalkyl-alkoxy group, an aralkyloxy group, an aralkyloxy-alkyl group, an alkylthio group, a cycloalkyl-alkylthio group, an amino group, a mono- or dialkylamino group, a cycloalkyl-alkylamino group, an acyl group, an acyloxy group, an oxo group, a carboxyl group, an alkoxycarbonyl group, an aralkyloxycarbonyl group, a carbamoyl group, a saturated or unsaturated heterocyclic group, an aromatic hydrocarbon group, and a saturated heterocyclic oxy group. When the above substituent is present, the number of the substituents is typically 1 to 3.

Examples of the halogen atom included in the substituent(s) include a chlorine atom, a bromine atom, a fluorine atom, and an iodine atom.

The alkyl group or the halogenoalkyl group included in the substituents preferably refers to a linear or branched alkyl group having 1 to 6 carbon atoms or a group in which one to all hydrogen atom(s) in such an alkyl group are substituted by the halogen atom described above. Examples thereof include alkyl groups such as a methyl group, an ethyl group, an n-propyl group, an isopropyl group, an n-butyl group, an isobutyl group, a sec-butyl group, a tert-butyl group, a pentyl group, and a hexyl group and halogenoalkyl groups such as a trifluoromethyl group.

The cycloalkyl group included in the substituents is preferably a cycloalkyl group having 3 to 7 carbon atoms, and examples thereof include a cyclopropyl group, a cyclobutyl group, a cyclopentyl group, a cyclohexyl group, and a cycloheptyl group.

The cycloalkyl-alkyl group included in the substituents is preferably an alkyl group having 1 to 6 carbon atoms which is substituted by cycloalkyl having 3 to 7 carbon atoms, and examples thereof include a cyclopropylmethyl group, a cyclopropylethyl group, a cyclobutylmethyl group, a cyclopentylmethyl group, and a cyclohexylmethyl group.

The aralkyl group included in the substituents preferably refers to a linear or branched alkyl group having 1 to 6 carbon atoms which is substituted by an aromatic hydrocarbon group having 6 to 14 carbon atoms, and examples thereof include a benzyl group, a phenylethyl group, a phenylpropyl group, a naphthylmethyl group, and a naphthylethyl group.

The hydroxyalkyl group included in the substituents preferably refers to the linear or branched alkyl group having 1 to 6 carbon atoms described above which has a hydroxy group, and examples thereof include a hydroxymethyl group and a hydroxyethyl group.

The alkenyl group included in the substituents preferably refers to an alkenyl group having 2 to 6 carbon atoms which contains a carbon-carbon double bond, and examples thereof include a vinyl group, an allyl group, a methylvinyl group, a propenyl group, a butenyl group, a pentenyl group, and a hexenyl group.

The alkynyl group included in the substituents preferably refers to an alkynyl group having 2 to 6 carbon atoms which contains a carbon-carbon triple bond, and examples thereof include an ethynyl group and a propargyl group.

The alkoxy group or the halogenoalkoxy group included in the substituents preferably refers to a linear or branched alkoxy group having 1 to 6 carbon atoms, or a group in which such an alkoxy group is substituted by the halogen atom described above, and examples thereof include a methoxy group, an ethoxy group, an n-propoxy group, an isopropoxy group, a 1-methylpropoxy group, an n-butoxy group, an isobutoxy group, a tert-butoxy group, a 2-methyl-butoxy group, a neopentyloxy group, a pentan-2-yloxy group, a fluoromethoxy group, a difluoromethoxy group, a trifluoromethoxy group, a 1,1-difluoroethoxy group, a 2,2-difluoroethoxy group, a 2,2,2-trifluoroethoxy group, a 1,1,2,2-tetrafluoroethoxy group, a perfluoroethoxy group, a 3-fluoro-2-(fluoromethyl)-propoxy group, a 1,3-difluoropropan-2-yloxy group, and a 2,2,3,3,3-pentafluoro-1-propoxy group.

The alkoxy-alkyl group included in the substituents preferably refers to the alkyl group having 1 to 6 carbon atoms described above which is substituted by the linear or branched alkoxy group having 1 to 6 carbon atoms described above, and examples thereof include a methoxymethyl group and an ethoxymethyl group.

The cycloalkoxy group included in the substituents is preferably a cycloalkoxy group having 3 to 7 carbon atoms, and examples thereof include a cyclopropoxy group, a cyclobutoxy group, a cyclopentyloxy group, a cyclohexyloxy group, and a cycloheptyloxy group.

The cycloalkyl-alkoxy group included in the substituents is preferably an alkoxy group having 1 to 6 carbon atoms which is substituted by cycloalkyl having 3 to 7 carbon atoms, and examples thereof include a cyclopropylmethoxy group, a cyclopropylethoxy group, a cyclobutylmethoxy group, a cyclopentylmethoxy group, and a cyclohexylmethoxy group.

The aralkyloxy group included in the substituents preferably refers to an oxy group which has the aralkyl group described above, and examples thereof include a benzyloxy group, a phenethyloxy group, a phenylpropyloxy group, a naphthylmethyloxy group, and a naphthylethyloxy group.

The aralkyloxy-alkyl group included in the substituents preferably refers to the linear or branched alkyl group having 1 to 6 carbon atoms described above which has the aralkyloxy group described above, and examples thereof include a benzyloxymethyl group and a benzyloxyethyl group.

The alkylthio group included in the substituents is preferably a (C1-C6) alkylthio group which refers to a linear or branched alkylthio group having 1 to 6 carbon atoms, and examples thereof include a methylthio group, an ethylthio group, an n-propylthio group, an isopropylthio group, an n-butylthio group, an isobutylthio group, a sec-butylthio group, a tert-butylthio group, a pentylthio group, and a hexylthio group.

The cycloalkyl-alkylthio group included in the substituents is preferably an alkylthio group having 1 to 6 carbon atoms which is substituted by cycloalkyl having 3 to 7 carbon atoms, and examples thereof include a cyclopropylmethylthio group, a cyclopropylethylthio group, a cyclobutylmethylthio group, a cyclopentylmethylthio group, and a cyclohexylmethylthio group.

The mono- or dialkylamino group included in the substituents is a mono- or di-(C1-C6 alkyl)amino group which refers to an amino group which is monosubstituted or disubstituted by the linear or branched alkyl group having 1 to 6 carbon atoms described above, and examples thereof include a methylamino group, a dimethylamino group, an ethylamino group, a diethylamino group, and a methylethylamino group.

The cycloalkyl-alkylamino group included in the substituents refers to an alkylamino group which is substituted by the cycloalkyl group described above, and examples thereof include a cyclopropylmethylamino group, a cyclobutylmethylamino group, and a cyclopentylmethylamino group.

Examples of the acyl group included in the substituents include: linear or branched acyl groups having 1 to 6 carbon atoms such as a formyl group, an acetyl group, a propionyl group, an n-butyryl group, an isobutyryl group, a valeryl group, an isovaleryl group, and a pivaloyl group; and a benzoyl group.

Examples of the acyloxy group included in the substituents include: linear or branched acyloxy groups having 1 to 6 carbon atoms such as a formyloxy group, an acetoxy group, a propionyloxy group, an n-butyryloxy group, an isobutyryloxy group, a valeryloxy group, an isovaleryloxy group, and a pivaloyloxy group; a benzoyloxy group; and amino acid-derived acyloxy groups such as a glycyloxy group, an alanyloxy group, and a leucyloxy group.

The alkoxycarbonyl group included in the substituents refers to a carbonyl group which is substituted by the alkoxy group described above, and examples thereof include a methoxycarbonyl group, an ethoxycarbonyl group, an n-propoxycarbonyl group, an isopropoxycarbonyl group, a 1-methylpropoxycarbonyl group, an n-butoxycarbonyl group, an isobutoxycarbonyl group, a tert-butoxycarbonyl group, a 2-methyl-butoxycarbonyl group, a neopentyloxycarbonyl group, and a pentan-2-yloxycarbonyl group.

The aralkyloxycarbonyl group included in the substituents preferably refers to a carbonyl group which is substituted by the aralkyloxy group described above, and examples thereof include a benzyloxycarbonyl group, a phenethyloxycarbonyl group, a phenylpropyloxycarbonyl group, a naphthylmethyloxycarbonyl group, and a naphthylethyloxycarbonyl group.

Examples of the carbamoyl group included in the substituents include a $-CONH_2$ group, a (mono- or dialkyl)carbamoyl group, a (mono- or diaryl)carbamoyl group, an (N-alkyl-N-aryl)carbamoyl group, a pyrrolidinocarbamoyl group, a piperidinocarbamoyl group, a piperazinocarbamoyl group, and a morpholinocarbamoyl group.

The saturated or unsaturated heterocyclic group included in the substituents refers to a mono- or hi-cyclic saturated or 5- to 10-membered unsaturated heterocyclic group preferably having 1 to 4 heteroatoms of any one of N, S and O, and examples thereof include a pyrrolidinyl group, a piperidinyl group, a piperazinyl group, a hexamethyleneimino group, a morpholino group, a thiomorpholino group, a homopiperazinyl group, a tetrahydrofuranyl group, a tetrahydropyranyl group, an imidazolyl group, a thienyl group, a furyl group, a pyrrolyl group, an oxazolyl group, an isoxazolyl group, a thiazolyl group, an isothiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a methylenedioxyphenyl group, an ethylenedioxyphenyl group, a benzofuranyl group, a dihydrobenzofuranyl group, a benzoimidazolyl group, a benzooxazolyl group, a benzothiazolyl group, a purinyl group, a quinolyl group, an isoquinolyl group, a quinazolinyl group, and a quinoxalyl group.

The aromatic hydrocarbon group included in the substituents preferably refers to an aromatic hydrocarbon group having 6 to 14 carbon atoms, and examples thereof include a phenyl group and a naphthyl group.

The saturated heterocyclic oxy group included in the substituents refers to a monocyclic 5- to 7-membered saturated heterocyclic group having one or two heteroatoms of any of N, S and O, for example, an oxy group which has a pyrrolidinyl group, a piperidinyl group, a piperazinyl group, a hexamethyleneimino group, a morpholino group, a thiomorpholino group, or a homopiperazinyl group. Examples thereof include a tetrahydrofuranyloxy group and a tetrahydropyranyloxy group.

In Formula (I), $X^1$ represents CH or N. Moreover, in Formula (I), any one of $X^2$, $X^3$, and $X^4$ represents N, and the others represent CH. Based on the definitions of $X^1$ to $X^4$, examples of the azabicyclo skeleton in Formula (I) include the following structures:

(A-1)

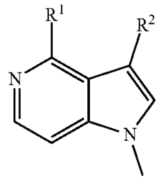

(A-2)

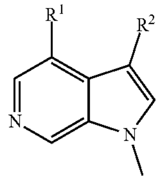

(A-3)

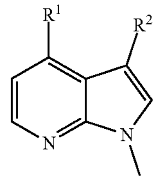

(A-4)

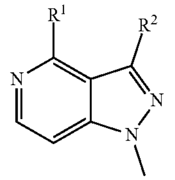

(A-5)

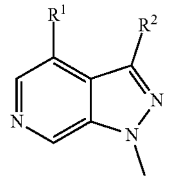

-continued (A-6)

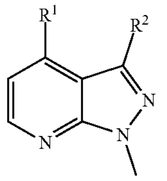

in the formula, $R^1$ and $R^2$ are as defined above.

Among these skeletons, (A-3) and (A-6) are particularly preferable.

In Formula (I), the "mono- or bi-cyclic unsaturated heterocyclic group having 1 to 4 heteroatoms selected from the group consisting of N, S, and O" in the "optionally substituted mono- or bi-cyclic unsaturated heterocyclic group having 1 to 4 heteroatoms selected from the group consisting of N, S, and O" represented by $R^1$ is preferably a mono- or bi-cyclic 5- to 10-membered unsaturated heterocyclic group having 1 to 3 heteroatoms selected from the group consisting of N, S, and O, more preferably a monocyclic 5- to 6-membered unsaturated heterocyclic group having 1 to 3 heteroatoms selected from the group consisting of N, S, and O, or a bicyclic 9- to 10-membered unsaturated heterocyclic group having 1 to 3 heteroatoms selected from the group consisting of N, S, and O.

The heterocyclic group is preferably a group having imidazole, pyrazole, thiophene, furan, pyrrole, oxazole, isoxazole, triazole, isothiazole, triazole, tetrazole, pyridine, pyrazine, pyrimidine, pyridazine, indole, isoindole, pyrrolopyridine, indazole, methylenedioxyphenyl, ethylenedioxyphenyl, benzofuran, dihydrobenzofuran, benzimidazol, benzoxazol, benzothiazole, purine, quinoline, tetrahydroquinoline, isoquinoline, quinazoline, or quinoxaline, more preferably a group having imidazol, pyrazol, thiophene, furan, pyridine, indole, pyrrolopyridine, benzofuran, quinoline, or tetrahydroquinoline, and particularly preferably a group having imidazol, pyridine, or quinoline.

Specific examples thereof include a 1H-imidazol-1-yl group, a 1H-imidazol-2-yl group, a 1H-imidazol-4-yl group, a 1H-pyrazol-1-yl group, a 1H-pyrazol-3-yl group, a 1H-pyrazol-4-yl group, a thiophen-2-yl group, a thiophen-3-yl group, a furan-2-yl group, a furan-3-yl group, a pyrrol-1-yl group, a pyrrol-2-yl group, a pyrrol-3-yl group, an oxazol-2-yl group, an oxazol-4-yl group, an oxazol-5-yl group, an isoxazol-3-yl group, an isoxazol-4-yl group, an isoxazol-5-yl group, a thiazol-2-yl group, a thiazol-3-yl group, a thiazol-4-yl group, a thiazol-5-yl group, an isothiazol-2-yl group, an isothiazol-4-yl group, an isothiazol-5-yl group, a pyrazol-1-yl group, a pyrazol-3-yl group, a pyrazol-4-yl group, a 1,2,3-triazol-1-yl group, a 1,2,3-triazol-4-yl group, a 1,2,4-triazol-1-yl group, a 1,2,4-triazol-3-yl group, a 1,2,4-triazol-4-yl group, a tetrazol-1-yl group, a tetrazol-5-yl group, a pyridin-2-yl group, a pyridin-3-yl group, a pyridin-4-yl group, a pyrazin-2-yl group, a pyrazin-3-yl group, a pyrimidin-2-yl group, a pyrimidin-4-yl group, a pyrimidin-5-yl group, a pyrimidin-6-yl group, a pyridazin-3-yl group, a pyridazin-4-yl group, an indol-1-yl group, an indol-2-yl group, an indol-3-yl group, an indol-4-yl group, an indol-5-yl group, an indol-6-yl group, an indol-7-yl group, an isoindol-1-yl group, an isoindol-2-yl group, an isoindol-4-yl group, an isoindol-5-yl group, a 1H-pyrrolo[2,3-b]pyridin-1-yl group, a 1H-pyrrolo[2,3-b]pyridin-2-yl group, a 1H-pyrrolo[2,3-b]pyridin-3-yl group, a 1H-pyrrolo[2,3-b]pyridin-4-yl group, a 1H-pyrrolo[2,3-b]pyridin-5-yl group, a 1H-pyrrolo[2,3-b]pyridin-6-yl group, a 1H-indazol- 1-yl group, a 1H-indazol-3-yl group, a 1H-indazol-4-yl group, a 1H-indazol-5-yl group, a 1H-indazol-6-yl group, a 1H-indazol-7-yl group, a methylenedioxyphenyl group, an ethylenedioxyphenyl group, a benzofuran-2-yl group, a benzofuran-3-yl group, a benzofuran-4-yl group, a benzofuran-5-yl group, a benzofuran-6-yl group, a benzofuran-7-yl group, a 2,3-dihydrobenzofuran-2-yl group, a 2,3-dihydrobenzofuran-3-yl group, a benzimidazol-1-yl group, a benzimidazol-2-yl group, a benzimidazol-4-yl group, a benzimidazol-5-yl group, a benzoxazol-2-yl group, a benzoxazol-4-yl group, a benzoxazol-5-yl group, a benzothiazol-2-yl group, a benzothiazol-4-yl group, a benzothiazol-5-yl group, a purin-2-yl group, a purin-6-yl group, a purin-7-yl group, a purin-8-yl group, a quinolin-2-yl group, quinolin-3-yl group, a quinolin-4-yl group, quinolin-5-yl group, a quinolin-6-yl group, a quinolin-7-yl group, a quinolin-8-yl group, a 5,6,7,8-tetrahydroquinolin-2-yl group, a 5,6,7,8-tetrahydroquinolin-3-yl group, a 5,6,7,8-tetrahydroquinolin-4-yl group, an isoquinolin-1-yl group, an isoquinolin-3-yl group, an isoquinolin-4-yl group, an isoquinolin-5-yl group, an isoquinolin-6-yl group, an isoquinolin-7-yl group, an isoquinolin-8-yl group, a quinazolin-4-yl group, a quinoxalin-2-yl group, a quinoxalin-5-yl group, and a quinoxalin-6-yl group. A 1H-imidazol-1-yl group, a pyrazol-4-yl group, a thiophen-3-yl group, a furan-2-yl group, a pyridin-3-yl group, a pyridin-4-yl group, an indol-5-yl group, a 1H-pyrrolo[2,3-b]pyridin-5-yl group, a benzofuran-2-yl group, a quinolin-3-yl group, and 5,6,7,8-tetrahydroquinolin-3-yl group are preferable, a 1H-imidazol-1-yl group, a pyridin-3-yl group, a pyridin-4-yl group, an indol-5-yl group, a 1H-pyrrolo[2,3-b]pyridin-5-yl group, a benzofuran-2-yl group, a quinolin-3-yl group, and a 5,6,7,8-tetrahydroquinolin-3-yl group are more preferable, and a 1H-imidazol-1-yl group, a pyridin-3-yl group, and a quinolin-3-yl group are particularly preferable.

In Formula (I), examples of the "substituent(s)" in the unsaturated heterocyclic group represented by $R^1$ include the substituents described above. The substituent(s) are preferably 1 to 3 substituents selected from the group consisting of an alkyl group, an alkoxy group, an alkoxy-alkyl group, an aralkyl group, an aralkyloxy-alkyl group, a halogen atom, a halogenoalkyl group, an acyl group, an optionally substituted saturated or unsaturated heterocyclic group, and an optionally substituted aromatic hydrocarbon group, more preferably 1 to 3 substituents selected from the group consisting of an alkyl group; an alkoxy group; an unsaturated heterocyclic group optionally having an alkyl group, a halogenoalkyl group, an aralkyl group, or a hydroxyalkyl group; and an aromatic hydrocarbon group optionally having an alkyl group, an alkoxy group, or a carbamoyl group. Herein, examples of the unsaturated heterocyclic group which may be substituted on the unsaturated heterocyclic ring represented by $R^1$ include pyrazol, imidazol, pyridine, pyrimidine, furan, and thiophene. In addition, examples of the aromatic hydrocarbon group include phenyl and naphthyl.

Specific examples of the "substituent(s)" in the unsaturated heterocyclic group represented by $R^1$ include a methyl group, an ethyl group, an n-propyl group, an isopropyl group, an n-butyl group, an isobutyl group, a sec-butyl group, a tert-butyl group, a methoxy group, an ethoxy group, an n-propoxy group, an isopropoxy group, a 1-methylpropoxy group, an n-butoxy group, an isobutoxy group, a tert-butoxy group, a 1H-pyrazol-4-yl group, a 1-methyl-1H-pyrazol-4-yl group, a 1-ethyl-1H-pyrazol-4-yl group, a 1-isopropyl-1H-pyrazol-4-yl group, a 1-benzyl-1H-pyrazol-4-yl group, a 1-(difluoromethyl)-1H-pyrazol-4-yl group, a 1-(hydroxyethyl)-1H-pyrazol-4-yl group, a 1H-imidazol-1-yl group, a pyridin-3-yl group, a pyridin-4-yl group, a pyrimidin-5-yl group, a furan-2-yl group, a furan-3-yl group, a thiophen-3-yl group, a phenyl group, a 4-methoxyphenyl group, a 4-carbamoylphenyl group, a 4-isopropylcarbamoylphenyl group, and a 4-dimethylcarbamoylphenyl group.

Specific examples of preferable $R^1$ include a 1H-imidazol-1-yl group, a 4-phenyl-1H-imidazol-1-yl group, a 4-(4-carbamoylphenyl)-1H-imidazol-1-yl group, a 4-(4-methoxyphenyl)-1H-imidazol-1-yl group, a 4-(thiophene-3-yl)-1H-imidazol-1-yl group, a 4-(pyridin-3-yl)-1H-imidazol-1-yl group, a 4-(pyridin-4-yl)-1H-imidazol-1-yl group, a 5-methyl-4-(pyridin-3-yl)-1H-imidazol-1-yl group, a 4-(pyrimidin-5-yl)-1H-imidazol-1-yl group, a 4-(furan-2-yl)-1H-imidazol-1-yl group, a 4-(furan-3-yl)-1H-imidazol-1-yl group, a 4-(1H-pyrazol-4-yl)-1H-imidazol-1-yl group, a 4-(1-methyl-1H-pyrazol-4-yl)-1H-imidazol-1-yl group, a 4-(l-ethyl-1H-pyrazol-4-yl)-1H-imidazol-1-yl group, a 4-(1-isopropyl-1H-pyrazol-4-yl)-1H-imidazol-1-yl group, a 4-(1-hydroxymethyl)-(1H-pyrazol-4-yl)-1H-imidazol-1-yl group, a 4-(1-(difluoromethyl)-1H-pyrazol-4-yl)-1H-imidazol-1-yl group, a 4-(1-(hydroxyethyl)-1H-pyrazol-4-yl)-1H-imidazol-1-yl group, a 4-(1-(hydroxymethyl)-1H-pyrazol-4-yl)-1H-imidazol-1-yl group, a 4-(1-benzyl-1H-pyrazol-4-yl)-1H-imidazol-1-yl group, a 4-(1-(benzyloxyethyl)-1H-pyrazol-4-yl)-1H-imidazol-1-yl group, a 1'H-1,4'-biimidazol-1'-yl group, a pyridin-3-yl group, a pyridin-4-yl group, a 5-methoxypyridin-3-yl group, a 6-methoxypyridin-3-yl group, a 1-benzyl-1H-pyrazol-4-yl group, a 1-methyl-1H-indol-5-yl group, a 1H-pyrrolo[2,3-b]pyridin-5-yl group, a 1-methyl-1H-pyrrolo[2,3-b]pyridin-5-yl group, a 1-methoxymethyl-1H-pyrrolo[2,3-b]pyridin-5-yl group, a 5,6,7,8-tetrahydroquinolin-3-yl group, a quinolin-3-yl group, a thiophen-3-yl group, a furan-2-yl group, and a benzofuran-2-yl group. $R^1$ is more preferably 1H-imidazol-1-yl group, a 4-(pyridin-3-yl)-1H-imidazol-1-yl group, a 4-(pyridin-4-yl)-1H-imidazol-1-yl group, a 4-(1H-pyrazol-4-yl)-1H-imidazol-1-yl group, a 4-(1-methyl-1H-pyrazol-4-yl)-1H-imidazol-1-yl group, a 4-(1-ethyl-1H-pyrazol-4-yl)-1H-imidazol-1-yl group, a 4-(1-isopropyl-1H-pyrazol-4-yl)-1H-imidazol-1-yl group, a 4-(1-benzyl-1H-pyrazol-4-yl)-1H-imidazol-1-yl group, a quinolin-3-yl group, or a 4-(1H-pyrazol-4-yl)-1H-imidazol-1-yl group, particularly preferably a 4-(1-methyl-1H-pyrazol-4-yl)-1H-imidazol-1-yl group, a 4-(pyridin-3-yl)-1H-imidazol-1-yl group, or a quinolin-3-yl group.

In Formula (I), the "alkyl group having 1 to 6 carbon atoms" in the "optionally substituted alkyl group having 1 to 6 carbon atoms" represented by $R^2$ refers to a linear or branched alkyl group having 1 to 6 carbon atoms, for example, a methyl group, an ethyl group, an n-propyl group, an isopropyl group, an n-butyl group, an isobutyl group, a sec-butyl group, a tert-butyl group, a pentyl group, or a hexyl group, and is preferably a methyl group, an ethyl group, an n-propyl group, or an isopropyl group.

Examples of the "substituent(s)" in the "optionally substituted alkyl group having 1 to 6 carbon atoms" represented by $R^2$ include the substituents described above. Among these substituents, halogen atoms are preferable.

The halogen atom-substituted alkyl group is preferably a halogenoalkyl group having 1 to 6 carbon atoms, more preferably a trifluoromethyl group.

The "alkenyl group having 2 to 6 carbon atoms" represented by $R^2$ refers to the alkenyl groups having 2 to 6 carbon atoms described above, and is preferably a vinyl group. Examples of the substituent(s) in the alkenyl group include the substituents described above.

$R^2$ is more preferably an optionally substituted alkyl group having 1 to 6 carbon atoms or an optionally substituted alkenyl group having 2 to 6 carbon atoms, even more preferably an alkyl group having 1 to 6 carbon atoms and optionally having a halogen atom, or an alkenyl group having 2 to 6 carbon atoms, particularly preferably an alkyl group having 1 to 4 carbon atoms and optionally having a halogen atom.

Any one or two of $Y^1$, $Y^2$, $Y^3$, and $Y^4$ are C—$R^4$, and the others are the same or different and represent CH or N. Preferably, any one or two of $Y^1$, $Y^2$, $Y^3$, and $Y^4$ are C—$R^4$, and the others are CH. More preferably, $Y^1$ and $Y^3$ are CH, any one or two of $Y^2$ and $Y^4$ are C—$R^4$, and the others are CH. These preferable aspects are represented by the following formulae:

(b1)

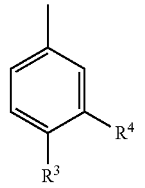

(b2)

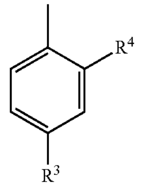

(b3)

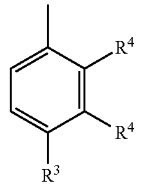

in the formula, $R^3$ and $R^4$ are as defined above.

Among these, (b1) and (b2) are particularly preferable.

In Formula (I), $R^3$ represents a cyano group or —CO—$R^5$. Among these, —CO—$R^5$ is particularly preferable.

In Formula (I), $R^4$(s) are the same or different and represent a hydrogen atom, a halogen atom, a cyano group, an optionally substituted alkyl group having 1 to 6 carbon atoms, an alkenyl group having 2 to 6 carbon atoms, an alkoxy group having 1 to 6 carbon atoms, an aromatic hydrocarbon group, —N($R^6$)($R^7$), —S$R^8$, or —CO—$R^9$. Among these, $R^4$ is preferably a halogen atom, an alkyl group having 1 to 6 carbon atoms and optionally having a mono- or di-(C1-C6 alkyl)amino group or a monocyclic 5- to 7-membered saturated heterocyclic group having one or two heteroatoms of any of N, S, and O, an alkoxy group having 1 to 6 carbon atoms, —N($R^6$)($R^7$), —S—$R^8$, or —CO—$R^9$, more preferably a halogen atom, an alkyl group having 1 to 6 carbon atoms, or —N($R^6$)($R^7$).

In Formula (I), the "halogen atom" represented by $R^4$ refers to the halogen atom described above and is preferably a chlorine atom.

In Formula (I), the "alkyl group having 1 to 6 carbon atoms" in the "optionally substituted alkyl group having 1 to 6 carbon atoms" represented by $R^4$ refers to the alkyl group having 1 to 6 carbon atoms described above and is preferably a methyl group, an ethyl group, an n-propyl group, or an isopropyl group.

Examples of the "substituent(s)" in the "optionally substituted alkyl group having 1 to 6 carbon atoms" represented by $R^4$ include the substituents described above. The "substituent(s)" are preferably mono- or di-(C1-C6 alkyl)amino groups such as an ethylamino group and a dimethylamino group or monocyclic 5- to 7-membered saturated heterocyclic groups having one or two heteroatoms of any of N, S, and O such as a pyrrolidyl group and morpholino group.

In Formula (I), the "alkenyl group having 2 to 6 carbon atoms" represented by $R^1$ refers to the alkenyl group having 2 to 6 carbon atoms and is preferably a vinyl group or a prop-1-en-2-yl group.

In Formula (I), the "alkoxy group having 1 to 6 carbon atoms" represented by $R^4$ refers to the alkoxy group having 1 to 6 carbon atoms and is preferably a methoxy group.

In Formula (I), the "mono- or di-alkylamino group" in the "optionally substituted mono- or di-alkylamino group" represented by $R^5$ refers to the mono- or dialkylamino group described above, and is preferably a mono- or di-(C1-C6 alkyl)amino group.

Examples of the "substituent(s)" in the "optionally substituted mono- or di-alkylamino group" represented by $R^5$ include the substituents described above.

$R^5$ is more preferably an amino group, a hydroxylamino group, or a mono- or di-(C1-C6 alkyl)amino group, particularly preferably an amino group.

In Formula (I), the "alkyl group having 1 to 6 carbon atoms" in the "optionally substituted alkyl group having 1 to 6 carbon atoms" represented by $R^6$ or $R^7$ refers to the alkyl group having 1 to 6 carbon atoms described above, and is preferably an ethyl group, an n-propyl group, an n-butyl group, an isobutyl group, a sec-butyl group, or a pentyl group.

Examples of the "substituent(s)" in the "optionally substituted alkyl group having 1 to 6 carbon atoms" represented by $R^6$ or $R^7$ include the substituents described above. The "substituent(s)" are preferably a hydroxyl group, cycloalkyl groups having 3 to 7 carbon atoms (for example, a cyclohexyl group), saturated heterocyclic groups (for example, a pyrrolidyl group and a morpholino group), unsaturated heterocyclic groups (for example, a pyridyl group), mono- or di-(C1-C6 alkyl)amino groups (for example, an ethylamino group and a dimethylamino group), (C1-C6 alkyl)thio groups (for example, a methylthio group), or alkoxy groups having 1 to 6 carbon atoms and optionally having a hydroxyl group.

In Formula (I), the "halogenoalkyl group having 1 to 6 carbon atoms" represented by $R^6$ or $R^7$ refers to the halogenoalkyl group having 1 to 6 carbon atoms described above, and is preferably a 2,2-difluoroethyl group or a 2,2,2-trifluoroethyl group.

In Formula (I), examples of the "cycloalkyl group having 3 to 7 carbon atoms" in the "optionally substituted cycloalkyl group having 3 to 7 carbon atoms" represented by $R^6$ or $R^7$ include a cyclopropyl group, a cyclobutyl group, a cyclopentyl group, a cyclohexyl group, and a cycloheptyl group, and is preferably a cyclopropyl group, a cyclopentyl group, or a cyclohexyl group.

Examples of the "substituent(s)" in the "optionally substituted cycloalkyl group having 3 to 7 carbon atoms" represented by $R^6$ or $R^7$ include the substituents described above. The substituent(s) are preferably a hydroxyl group, an amino group, an amino acid group-derived acyloxy group, an alkanoylamino group, or an alkylsulfonylamino group.

In Formula (I), the "aralkyl group" in the "optionally substituted aralkyl group" represented by $R^6$ or $R^7$ refers to the aralkyl group described above, and is preferably an aralkyl group having 7 to 12 carbon atoms, specifically, a benzyl group.

Examples of the "substituent(s)" in the "optionally substituted aralkyl group" represented by $R^6$ or $R^7$ include the substituents described above. Specific examples of the substituent(s) include saturated heterocyclic groups such as a pyrrolidinyl group.

In Formula (I), the "aromatic hydrocarbon group" in the "optionally substituted aromatic hydrocarbon group" represented by $R^6$ or $R^7$ refers to the aromatic hydrocarbon group having 6 to 14 of carbon atom described above, and is preferably a phenyl group. Examples of the "substituent(s)" in the "optionally substituted aromatic hydrocarbon group" represented by $R^6$ or $R^7$ include the substituents described above. The substituent(s) are preferably halogen atoms, alkylthio groups (for example, a methylthio group), saturated heterocyclic groups (for example, a morpholino group), or substituted carbamoyl groups (for example, a pyrrolidine-carbonyl group).

In the Formula (I), the "saturated heterocyclic group" in the "optionally substituted saturated heterocyclic group" represented by $R^6$ or $R^7$ refers to the saturated heterocyclic group described above, and is preferably a piperidinyl group or a tetrahydropyranyl group.

Examples of the "substituent(s)" in the "optionally substituted saturated heterocyclic group" represented by $R^6$ or $R^7$ include the substituents described above. The substituent(s) are preferably alkyl groups having 1 to 6 carbon atoms (for example, a methyl group), acyl groups (for example, an acetyl group), carbonyl groups having a saturated heterocyclic group (for example, a 2,6-dihydroxypyrimidinyl-4-carbonyl group), or aminoalkylcarbonyl groups (for example, a 2-aminoacetyl group).

In Formula (I), the "unsaturated heterocyclic group" in the "optionally substituted unsaturated heterocyclic group" represented by $R^6$ or $R^7$ refers to the unsaturated heterocyclic group described above, and is preferably a pyridyl group or an oxazolyl group.

Examples of the "substituent(s)" in the "optionally substituted unsaturated heterocyclic group" represented by $R^6$ or $R^7$ include the substituents described above.

In Formula (I), the "saturated heterocyclic group" which is optionally formed by $R^6$ and $R^7$ together with the nitrogen atom to which they are bonded refers to a mono- or bi-cyclic saturated heterocyclic group preferably having 1 to 4 atoms of any of oxygen, nitrogen, and sulfur, and for example, a pyrrolidinyl group, a piperidinyl group, a piperazinyl group, a hexamethyleneimino group, a morpholino group, a thiomorpholino group, a homopiperazinyl group, a tetrahydrofuranyl group, or tetrahydropyranyl group.

In Formula (I), it is preferred for the combination of $R^6$ and $R^7$ that $R^6$ be a hydrogen atom or an optionally substituted alkyl group having 1 to 6 carbon atoms; and $R^7$ represent a hydrogen atom, an optionally substituted alkyl group having 1 to 6 carbon atoms, an optionally substituted cycloalkyl group having 3 to 7 carbon atoms, an optionally substituted aralkyl group having 7 to 12 carbon atoms, an optionally substituted aromatic hydrocarbon group having 6 to 14 carbon atoms, an optionally substituted mono- or bi-cyclic saturated heterocyclic group having 1 to 4 heteroatoms selected from the group consisting of N, S, and O, or an optionally substituted mono- or bi-cyclic unsaturated heterocyclic group having 1 to 4 heteroatoms selected from the group consisting of N, S, and O, or $R^6$ and $R^7$ optionally form a 5- to 7-membered saturated heterocyclic group, together with the nitrogen atom to which they are bonded. More preferably, $R^6$ is a hydrogen atom, and R' is a hydrogen atom, an optionally substituted alkyl group having 1 to 6 carbon atoms, an optionally substituted cycloalkyl group having 3 to 7 carbon atoms, or an optionally substituted mono- or bi-cyclic saturated heterocyclic group having 1 to 4 heteroatoms selected from the group consisting of N, S, and O. Particularly preferably, $R^6$ is a hydrogen atom, and $R^7$ is an optionally substituted alkyl group having 1 to 6 carbon atoms or an optionally substituted cycloalkyl group having 3 to 7 carbon atoms.

In Formula (I), the "cycloalkyl group having 3 to 7 carbon atoms" in the "optionally substituted cycloalkyl group having 3 to 7 carbon atoms" represented by $R^8$ refers to the cycloalkyl group having 3 to 7 carbon atoms described above, and is preferably a cyclohexyl group.

Examples of the "substituent(s)" in the "optionally substituted cycloalkyl group having 3 to 7 carbon atoms" represented by $R^8$ include the substituents described above. The substituent(s) are preferably a hydroxyl group.

In Formula (I), the "aromatic hydrocarbon group" in the "optionally substituted aromatic hydrocarbon group" represented by $R^8$ refers to the aromatic hydrocarbon group having 6 to 14 carbon atoms described above, and is preferably a phenyl group.

Examples of the "substituent(s)" in the "optionally substituted aromatic hydrocarbon group" represented by $R^8$ include the substituents described above. The substituent(s) are preferably a hydroxyl group.

$R^8$ is preferably an optionally substituted cycloalkyl group having 3 to 7 carbon atoms, or an optionally substituted aromatic hydrocarbon group having 6 to 14 carbon atoms.

In Formula (I), the "mono- or di-alkylamino group" in the "optionally substituted mono- or di-alkylamino group" represented by $R^9$ refers to the mono- or dialkylamino group described above, and is preferably a mono- or di-(C1-C6 alkyl)amino group.

Examples of the "substituent(s)" in the "optionally substituted mono- or di-alkylamino group" represented by $R^9$ include the substituents described above.

$R^9$ is preferably a hydrogen atom, a hydroxyl group, an amino group or a mono- or di-(C1-C6 alkyl)amino group, particularly preferably a hydrogen atom.

The preferred azabicyclo compound of the present invention is a compound of Formula (I), where $X^1$ is CH or N; $X^2$ is N and $X^3$ and $X^4$ are CH; $Y^1$ and $Y^3$ are CH, any one or two of $Y^2$ and $Y^4$ are C—$R^4$, and the other is CH; $R^4$ is any of an optionally substituted 1H-imidazol-1-yl group, an optionally substituted pyrazol-4-yl group, an optionally substituted thiophen-3-yl group, an optionally substituted furan-2-yl group, an optionally substituted pyridin-3-yl group, an optionally substituted pyridin-4-yl group, an optionally substituted indol-5-yl group, an optionally substituted 1H-pyrrolo[2,3-b]pyridin-5-yl group, an optionally substituted benzofuran-2-yl group, an optionally substituted quinolin-3-yl group, and an optionally substituted 5,6,7,8-tetrahydroquinolin-3-yl group; $R^2$ is an alkyl group having 1 to 6 carbon atoms and optionally having a halogen atom or an alkenyl group having 2 to 6 carbon atoms; $R^3$ is —CO—$R^5$; $R^4$ is a halogen atom, an alkyl group having 1 to 6 carbon atoms and optionally having a mono- or di-(C1-C6 alkyl)amino group or a monocyclic 5- to 7-membered saturated heterocyclic group having one or two heteroatoms of any of N, S, and O, an alkoxy group having 1 to 6 carbon atoms, —N($R^6$)($R^7$), —S—$R^8$, or —CO—$R^9$; $R^5$ is an amino group or mono- or di-(C1-C6 alkyl)amino group; $R^6$ is a hydrogen atom or an optionally substituted alkyl group having 1 to 6 carbon atoms; $R^7$ is a hydrogen atom, an optionally substituted alkyl group having 1 to 6 carbon atoms, an optionally substituted cycloalkyl group having 3 to 7 carbon atoms, an optionally substituted aralkyl group having 7 to 12 carbon atoms, an optionally substituted aromatic hydrocarbon group having 6 to 14 carbon atoms, an optionally substituted mono- or bi-cyclic saturated heterocyclic group having 1 to 4 heteroatoms selected from the group consisting of N, S, and O, or an optionally substituted mono- or bi-cyclic unsaturated heterocyclic group having 1 to 4 heteroatoms selected from the group consisting of N, S, and O, or $R^6$ and $R^7$ form a 5- to 7-membered saturated heterocyclic group together with a nitrogen atom to which they are bonded; $R^8$ is an optionally substituted cycloalkyl group having 3 to 7 carbon atoms or an optionally substituted aromatic hydrocarbon group having 6 to 14 carbon atoms; and $R^9$ is a hydrogen atom, a hydroxyl group, an amino group, or a mono- or di-(C1-C6 alkyl)amino group.

More specifically, the azabicyclo compound is 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide (hereinafter, referred to as Compound 1).

The salt of the azabicyclo compound of the present invention is not particularly limited as long as it is a pharmaceutically acceptable salt, and examples thereof include acid addition salts of inorganic acids (for example, hydrochloric acid, hydrobromic acid, hydroiodic acid, sulfuric acid, nitric acid, and phosphoric acid) and organic acids (for example, formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, p-toluenesulfonic acid, and glutamic acid); salts of inorganic bases (for example, sodium, potassium, magnesium, calcium, and aluminum), organic bases (for example, methylamine, ethylamine, meglumine, and ethanolamine), or a basic amino acids (for example, lysine, arginine, and ornithine); and ammonium salts.

The azabicyclo compound of the present invention or a salt thereof can be synthesized according to the method described in WO 2011/004610 A, for example.

The azabicyclo compound of the present invention or a salt thereof, when administered in combination with a PARP inhibitor, synergistically potentiates an antitumor effect as shown in Examples described below.

In the present invention, the “PARP inhibitor” is a molecular targeting drug having action of selectively inhibiting poly(adenosine 5'-diphosphate-ribose) polymerase (PARP), a primary enzyme of DNA single-strand break repair.

Specific examples of the PARP inhibitor include olaparib (AZD2281), rucaparib (AG-014699), talazoparib (BMN673), veliparib (ABT-888), iniparib (BSI-201), 4-hydroxyquinazoline, pamiparib (BGB-290), AG-14361, INO-1001, A-966492, PJ34 HCl, niraparib (MK-4827), UPF1069, AZD2461, ME0328, BGP-15 2HCl, niraparib (MK-4827) tosylate, NU1025, G007-LK, NVP-TNKS656, E7449, NMS-P118, benzamide, and picolinamide from the viewpoint of a synergistic action on an antitumor effect when the azabicyclo compound of the present invention or a salt thereof is used in combination. Among them, one or more selected from the group consisting of olaparib (AZD2281), rucaparib (AG-014699), talazoparib (BMN673), veliparib (ABT-888), iniparib (BSI-201), pamiparib (BGB-290), niraparib (MK-4827) and niraparib (MK-4827) tosylate are more preferable, and one or more selected from the group consisting of olaparib (AZD2281), rucaparib (AG-014699), talazoparib (BMN673), niraparib (MK-4827) and veliparib (ABT-888) are particularly preferable.

In the present invention, the dosage of the azabicyclo compound of Formula (I) or a salt thereof per administration day is preferably from 50 to 200%, more preferably from 50 to 112.5%, particularly preferably from 50% to 100%, of a recommended dosage for the administration of the azabicyclo compound of Formula (I) or a salt thereof alone from the viewpoint of the potentiating effect of the azabicyclo compound of Formula (I) on the antitumor effect of the PARP inhibitor. The recommended dosage in a human is preferably from 40 to 320 mg/body/day, more preferably from 40 to 200 mg/body/day, particularly preferably from 40 mg/body/day to 160 mg/body/day. Specifically, 40/body/day, 80 mg/body/day, 120 mg/body/day, and 160 mg/body/day are preferable, and 160 mg/body/day is further preferable.

In the present invention, the dosage of the PARP inhibitor per administration day is preferably from 50 to 200%, more preferably from 100%, of a recommended dosage for the administration of the PARP inhibitor alone from the viewpoint of the potentiating effect of the azabicyclo compound of Formula (I) on the antitumor effect of the PARP inhibitor.

In one embodiment of the present disclosure, the dosage of the azabicyclo compound of Formula (I) or a salt thereof can be decreased to 120 mg/body/day, 80 mg/body/day, or 40 mg/body/day.

Specifically, the recommended dosage of olaparib to be administered alone to an adult human is usually 600 mg/day which is a dosage approved in Japan or 800 mg/day which is a dosage approved in the United State and the Europe. In a usual administration method, 300 mg is administered twice a day when the daily dosage is 600 mg. The dosage may be increased or decreased, if necessary. A preferable daily dosage is from 100 mg to 1,000 mg, preferably from 250 mg to 650 mg, particularly preferably from 600 mg or 800 mg.

The recommended dosage of rucaparib to be administered alone to an adult human is usually 600 mg/day. In a usual administration method, 300 mg is administered twice a day. The dosage may be increased or decreased, if necessary. A preferable daily dosage is from 200 mg to 1,000 mg, preferably from 200 mg to 800 mg, particularly preferably 600 mg.

The recommended dosage of talazoparib to be administered alone to an adult human is usually 1 mg/day. In a usual administration method, 1 mg is administered once a day. The dosage may be increased or decreased, if necessary. A preferable daily dosage is from 0.25 mg to 2 mg, preferably from 0.25 mg to 1.50 mg, particularly preferably from 1 mg or 0.75 mg, still further preferably 1 mg.

The recommended dosage of niraparib to be administered alone to an adult human is usually 300 mg/day. In a usual administration method, 300 mg is administered once a day. The dosage may be increased or decreased, if necessary. A preferable daily dosage is from 100 mg to 300 mg, particularly preferably 300 mg.

The recommended dosage of veliparib to be administered alone to an adult human is usually 800 mg/day. In a usual administration method, 400 mg is administered twice a day. The dosage may be increased or decreased, if necessary. A preferable daily dosage is from 200 mg to 1,000 mg, further preferably from 200 to 800 mg, still further preferably 800 mg.

In the present invention, the "recommended dosage", which is determined through a clinical trial or the like, is a dosage at which the maximum therapeutic effect is exhibited while safe use is assured without development of a serious side effect. Specific examples of the recommended dosage include dosages approved, recommended or suggested by public organizations such as Pharmaceuticals and Medical Devices Agency (PMDA), Food and Drug Administration (FDA) and European Medicines Agency (EMA), or corporations, and described in appended documents, interview forms, treatment guidelines or the like, and dosages approved by any of the public organizations which are PMDA, FDA and EMA are preferable.

The schedules of administration of the azabicyclo compound of Formula (I) of the present invention or the salt thereof and the PARP inhibitor may be appropriately selected in accordance with the type of a cancer, the stage of the disease, etc.

For the schedule of administration of the azabicyclo compound of Formula (I) or the salt thereof, it is preferred to repeat 5-day continuous administration and 2-day drug holiday, specifically, to repeat each cycle involving administration for 3 weeks using an administration method of 5-day administration followed by 2-day drug holiday per week.

Another schedule of administration of the azabicyclo compound of Formula (I) or the salt thereof is preferably everyday administration or alternate-day administration, most preferably everyday administration.

For the PARP inhibitor, the schedule of administration recommended for each PAPR inhibitor is preferable. The schedules of administration of olaparib, rucaparib, talazoparib, niraparib, and veliparib are preferably everyday administration or alternate-day administration, most preferably everyday administration.

The numbers of daily doses of the azabicyclo compound of Formula (I) of the present invention or the salt thereof and the PARP inhibitor may be appropriately selected in accordance with the type of a cancer, the stage of the disease, etc.

The azabicyclo compound of Formula (I) or the salt thereof is preferably administered once a day or twice a day, more preferably once a day. Olaparib is preferably administered once a day or twice a day, more preferably twice a day. Rucaparib is preferably administered once a day or twice a day, more preferably twice a day. Talazoparib is preferably administered once a day or twice a day, more preferably once a day. Niraparib is preferably administered once a day or twice a day, more preferably once a day. Veliparib is preferably administered once a day or twice a day, more preferably twice a day.

The order of administration of the azabicyclo compound of Formula (I) or the salt thereof and the PARP inhibitor may be appropriately selected in accordance with the type of a cancer, the stage of the disease, etc. Either of them may be administered first, or both of them may be concurrently administered. Herein, the administration interval between both the agents, when the agents are not concurrently administered, may be appropriately selected as long as an effect of potentiating an antitumor effect is exerted. The administration interval is preferably 1 to 14 days, more preferably 1 to 7 days, more preferably 1 to 5 days, particularly preferably 1 to 3 days.

In the present invention, examples of the combination of the dosage of the azabicyclo compound of Formula (I) or the salt thereof per day and the dosage of the PARP inhibitor per day, usually in an adult human, include the following.

40 to 320 mg of the azabicyclo compound of Formula (I) or the salt thereof and 100 mg to 1,000 mg of olaparib.

40 to 200 mg of the azabicyclo compound of Formula (I) or the salt thereof and 100 mg of olaparib.

40 to 200 mg of the azabicyclo compound of Formula (I) or the salt thereof and 200 mg of olaparib.

40 to 200 mg of the azabicyclo compound of Formula (I) or the salt thereof and 300 mg of olaparib.

40 to 200 mg of the azabicyclo compound of Formula (I) or the salt thereof and 400 mg of olaparib.

40 to 200 mg of the azabicyclo compound of Formula (I) or the salt thereof and 500 mg of olaparib.

40 to 200 mg of the azabicyclo compound of Formula (I) or the salt thereof and 600 mg of olaparib.

40 to 200 mg of the azabicyclo compound of Formula (I) or the salt thereof and 700 mg of olaparib.

40 to 200 mg of the azabicyclo compound of Formula (I) or the salt thereof and 800 mg of olaparib.

40 to 200 mg of the azabicyclo compound of Formula (I) or the salt thereof and 900 mg of olaparib.

40 to 200 mg of the azabicyclo compound of Formula (I) or the salt thereof and 1,000 mg of olaparib.

40 mg of the azabicyclo compound of Formula (I) or the salt thereof and 100 mg to 1,000 mg of olaparib.

40 mg of the azabicyclo compound of Formula (I) or the salt thereof and 100 mg of olaparib.

40 mg of the azabicyclo compound of Formula (I) or the salt thereof and 200 mg of olaparib.

40 mg of the azabicyclo compound of Formula (I) or the salt thereof and 300 mg of olaparib.

40 mg of the azabicyclo compound of Formula (I) or the salt thereof and 400 mg of olaparib.

40 mg of the azabicyclo compound of Formula (I) or the salt thereof and 500 mg of olaparib.

40 mg of the azabicyclo compound of Formula (I) or the salt thereof and 600 mg of olaparib.

40 mg of the azabicyclo compound of Formula (I) or the salt thereof and 700 mg of olaparib.

40 mg of the azabicyclo compound of Formula (I) or the salt thereof and 800 mg of olaparib.

40 mg of the azabicyclo compound of Formula (I) or the salt thereof and 900 mg of olaparib.

40 mg of the azabicyclo compound of Formula (I) or the salt thereof and 1,000 mg of olaparib.

80 mg of the azabicyclo compound of Formula (I) or the salt thereof and 100 mg of olaparib.

80 mg of the azabicyclo compound of Formula (I) or the salt thereof and 200 mg of olaparib.

80 mg of the azabicyclo compound of Formula (I) or the salt thereof and 300 mg of olaparib.

80 mg of the azabicyclo compound of Formula (I) or the salt thereof and 400 mg of olaparib.

80 mg of the azabicyclo compound of Formula (I) or the salt thereof and 500 mg of olaparib.

80 mg of the azabicyclo compound of Formula (I) or the salt thereof and 600 mg of olaparib.

80 mg of the azabicyclo compound of Formula (I) or the salt thereof and 700 mg of olaparib.

80 mg of the azabicyclo compound of Formula (I) or the salt thereof and 800 mg of olaparib.

80 mg of the azabicyclo compound of Formula (I) or the salt thereof and 900 mg of olaparib.

80 mg of the azabicyclo compound of Formula (I) or the salt thereof and 1,000 mg of olaparib.

120 mg of the azabicyclo compound of Formula (I) or the salt thereof and 100 mg of olaparib.

120 mg of the azabicyclo compound of Formula (I) or the salt thereof and 200 mg of olaparib.

120 mg of the azabicyclo compound of Formula (I) or the salt thereof and 300 mg of olaparib.

120 mg of the azabicyclo compound of Formula (I) or the salt thereof and 400 mg of olaparib.

120 mg of the azabicyclo compound of Formula (I) or the salt thereof and 500 mg of olaparib.

120 mg of the azabicyclo compound of Formula (I) or the salt thereof and 600 mg of olaparib.

120 mg of the azabicyclo compound of Formula (I) or the salt thereof and 700 mg of olaparib.

120 mg of the azabicyclo compound of Formula (I) or the salt thereof and 800 mg of olaparib.

120 mg of the azabicyclo compound of Formula (I) or the salt thereof and 900 mg of olaparib.

120 mg of the azabicyclo compound of Formula (I) or the salt thereof and 1,000 mg of olaparib.

160 mg of the azabicyclo compound of Formula (I) or the salt thereof and 100 mg of olaparib.

160 mg of the azabicyclo compound of Formula (I) or the salt thereof and 200 mg of olaparib.

160 mg of the azabicyclo compound of Formula (I) or the salt thereof and 300 mg of olaparib.

160 mg of the azabicyclo compound of Formula (I) or the salt thereof and 400 mg of olaparib.

160 mg of the azabicyclo compound of Formula (I) or the salt thereof and 500 mg of olaparib.

160 mg of the azabicyclo compound of Formula (I) or the salt thereof and 600 mg of olaparib.

160 mg of the azabicyclo compound of Formula (I) or the salt thereof and 700 mg of olaparib.

160 mg of the azabicyclo compound of Formula (I) or the salt thereof and 800 mg of olaparib.

160 mg of the azabicyclo compound of Formula (I) or the salt thereof and 900 mg of olaparib.

160 mg of the azabicyclo compound of Formula (I) or the salt thereof and 1,000 mg of olaparib.

200 mg of the azabicyclo compound of Formula (I) or the salt thereof and 100 mg of olaparib.

200 mg of the azabicyclo compound of Formula (I) or the salt thereof and 200 mg of olaparib.

200 mg of the azabicyclo compound of Formula (I) or the salt thereof and 300 mg of olaparib.

200 mg of the azabicyclo compound of Formula (I) or the salt thereof and 400 mg of olaparib.

200 mg of the azabicyclo compound of Formula (I) or the salt thereof and 500 mg of olaparib.

200 mg of the azabicyclo compound of Formula (I) or the salt thereof and 600 mg of olaparib.

200 mg of the azabicyclo compound of Formula (I) or the salt thereof and 700 mg of olaparib.

200 mg of the azabicyclo compound of Formula (I) or the salt thereof and 800 mg of olaparib.

200 mg of the azabicyclo compound of Formula (I) or the salt thereof and 900 mg of olaparib.

200 mg of the azabicyclo compound of Formula (I) or the salt thereof and 1,000 mg of olaparib.

40 to 320 mg of the azabicyclo compound of Formula (I) or the salt thereof and 200 mg to 800 mg of rucaparib.

40 to 200 mg of the azabicyclo compound of Formula (I) or the salt thereof and 200 mg of rucaparib.

40 to 200 mg of the azabicyclo compound of Formula (I) or the salt thereof and 300 mg of rucaparib.

40 to 200 mg of the azabicyclo compound of Formula (I) or the salt thereof and 400 mg of rucaparib.

40 to 200 mg of the azabicyclo compound of Formula (I) or the salt thereof and 500 mg of rucaparib.

40 to 200 mg of the azabicyclo compound of Formula (I) or the salt thereof and 600 mg of rucaparib.

40 to 200 mg of the azabicyclo compound of Formula (I) or the salt thereof and 700 mg of rucaparib.

40 to 200 mg of the azabicyclo compound of Formula (I) or the salt thereof and 800 mg of rucaparib.

40 mg of the azabicyclo compound of Formula (I) or the salt thereof and 200 mg of rucaparib.

40 mg of the azabicyclo compound of Formula (I) or the salt thereof and 300 mg of rucaparib.

40 mg of the azabicyclo compound of Formula (I) or the salt thereof and 400 mg of rucaparib.

40 mg of the azabicyclo compound of Formula (I) or the salt thereof and 500 mg of rucaparib.

40 mg of the azabicyclo compound of Formula (I) or the salt thereof and 600 mg of rucaparib.

40 mg of the azabicyclo compound of Formula (I) or the salt thereof and 700 mg of rucaparib.

40 mg of the azabicyclo compound of Formula (I) or the salt thereof and 800 mg of rucaparib.

80 mg of the azabicyclo compound of Formula (I) or the salt thereof and 200 mg of rucaparib.

80 mg of the azabicyclo compound of Formula (I) or the salt thereof and 300 mg of rucaparib.

80 mg of the azabicyclo compound of Formula (I) or the salt thereof and 400 mg of rucaparib.

80 mg of the azabicyclo compound of Formula (I) or the salt thereof and 500 mg of rucaparib.

80 mg of the azabicyclo compound of Formula (I) or the salt thereof and 600 mg of rucaparib.

80 mg of the azabicyclo compound of Formula (I) or the salt thereof and 700 mg of rucaparib.

80 mg of the azabicyclo compound of Formula (I) or the salt thereof and 800 mg of rucaparib.

120 mg of the azabicyclo compound of Formula (I) or the salt thereof and 200 mg of rucaparib.

120 mg of the azabicyclo compound of Formula (I) or the salt thereof and 300 mg of rucaparib.

120 mg of the azabicyclo compound of Formula (I) or the salt thereof and 400 mg of rucaparib.

120 mg of the azabicyclo compound of Formula (I) or the salt thereof and 500 mg of rucaparib.

120 mg of the azabicyclo compound of Formula (I) or the salt thereof and 600 mg of rucaparib.

120 mg of the azabicyclo compound of Formula (I) or the salt thereof and 700 mg of rucaparib.

120 mg of the azabicyclo compound of Formula (I) or the salt thereof and 800 mg of rucaparib.

160 mg of the azabicyclo compound of Formula (I) or the salt thereof and 200 mg of rucaparib.

160 mg of the azabicyclo compound of Formula (I) or the salt thereof and 300 mg of rucaparib.

160 mg of the azabicyclo compound of Formula (I) or the salt thereof and 400 mg of rucaparib.

160 mg of the azabicyclo compound of Formula (I) or the salt thereof and 500 mg of rucaparib.

160 mg of the azabicyclo compound of Formula (I) or the salt thereof and 600 mg of rucaparib.

160 mg of the azabicyclo compound of Formula (I) or the salt thereof and 700 mg of rucaparib.

160 mg of the azabicyclo compound of Formula (I) or the salt thereof and 800 mg of rucaparib.

200 mg of the azabicyclo compound of Formula (I) or the salt thereof and 200 mg of rucaparib.

200 mg of the azabicyclo compound of Formula (I) or the salt thereof and 300 mg of rucaparib.

200 mg of the azabicyclo compound of Formula (I) or the salt thereof and 400 mg of rucaparib.

200 mg of the azabicyclo compound of Formula (I) or the salt thereof and 500 mg of rucaparib.

200 mg of the azabicyclo compound of Formula (I) or the salt thereof and 600 mg of rucaparib.

200 mg of the azabicyclo compound of Formula (I) or the salt thereof and 700 mg of rucaparib.

200 mg of the azabicyclo compound of Formula (I) or the salt thereof and 800 mg of rucaparib.

40 to 320 mg of the azabicyclo compound of Formula (I) or the salt thereof and 0.25 mg to 2 mg of talazoparib.

40 to 200 mg of the azabicyclo compound of Formula (I) or the salt thereof and 0.25 mg of talazoparib.

40 to 200 mg of the azabicyclo compound of Formula (I) or the salt thereof and 0.5 mg of talazoparib.

40 to 200 mg of the azabicyclo compound of Formula (I) or the salt thereof and 0.75 mg of talazoparib.

40 to 200 mg of the azabicyclo compound of Formula (I) or the salt thereof and 1 mg of talazoparib.

40 to 200 mg of the azabicyclo compound of Formula (I) or the salt thereof and 1.25 mg of talazoparib.

40 to 200 mg of the azabicyclo compound of Formula (I) or the salt thereof and 1.50 mg of talazoparib.

40 to 200 mg of the azabicyclo compound of Formula (I) or the salt thereof and 2 mg of talazoparib.

40 mg of the azabicyclo compound of Formula (I) or the salt thereof and 0.25 mg of talazoparib.

40 mg of the azabicyclo compound of Formula (I) or the salt thereof and 0.5 mg of talazoparib.

40 mg of the azabicyclo compound of Formula (I) or the salt thereof and 0.75 mg of talazoparib.

40 mg of the azabicyclo compound of Formula (I) or the salt thereof and 1 mg of talazoparib.

40 mg of the azabicyclo compound of Formula (I) or the salt thereof and 1.25 mg of talazoparib.

40 mg of the azabicyclo compound of Formula (I) or the salt thereof and 1.50 mg of talazoparib.

40 mg of the azabicyclo compound of Formula (I) or the salt thereof and 2 mg of talazoparib.

80 mg of the azabicyclo compound of Formula (I) or the salt thereof and 0.25 mg of talazoparib.

80 mg of the azabicyclo compound of Formula (I) or the salt thereof and 0.5 mg of talazoparib.

80 mg of the azabicyclo compound of Formula (I) or the salt thereof and 0.75 mg of talazoparib.

80 mg of the azabicyclo compound of Formula (I) or the salt thereof and 1 mg of talazoparib.

80 mg of the azabicyclo compound of Formula (I) or the salt thereof and 1.25 mg of talazoparib.

80 mg of the azabicyclo compound of Formula (I) or the salt thereof and 1.50 mg of talazoparib.

80 mg of the azabicyclo compound of Formula (I) or the salt thereof and 2 mg of talazoparib.

120 mg of the azabicyclo compound of Formula (I) or the salt thereof and 0.25 mg of talazoparib.

120 mg of the azabicyclo compound of Formula (I) or the salt thereof and 0.5 mg of talazoparib.

120 mg of the azabicyclo compound of Formula (I) or the salt thereof and 0.75 mg of talazoparib.

120 mg of the azabicyclo compound of Formula (I) or the salt thereof and 1 mg of talazoparib.

120 mg of the azabicyclo compound of Formula (I) or the salt thereof and 1.25 mg of talazoparib.

120 mg of the azabicyclo compound of Formula (I) or the salt thereof and 1.50 mg of talazoparib.

120 mg of the azabicyclo compound of Formula (I) or the salt thereof and 2 mg of talazoparib.

160 mg of the azabicyclo compound of Formula (I) or the salt thereof and 0.25 mg of talazoparib.

160 mg of the azabicyclo compound of Formula (I) or the salt thereof and 0.5 mg of talazoparib.

160 mg of the azabicyclo compound of Formula (I) or the salt thereof and 0.75 mg of talazoparib.

160 mg of the azabicyclo compound of Formula (I) or the salt thereof and 1 mg of talazoparib.

160 mg of the azabicyclo compound of Formula (I) or the salt thereof and 1.25 mg of talazoparib.

160 mg of the azabicyclo compound of Formula (I) or the salt thereof and 1.50 mg of talazoparib.

160 mg of the azabicyclo compound of Formula (I) or the salt thereof and 2 mg of talazoparib.

200 mg of the azabicyclo compound of Formula (I) or the salt thereof and 0.25 mg of talazoparib.

200 mg of the azabicyclo compound of Formula (I) or the salt thereof and 0.5 mg of talazoparib.

200 mg of the azabicyclo compound of Formula (I) or the salt thereof and 0.75 mg of talazoparib.

200 mg of the azabicyclo compound of Formula (I) or the salt thereof and 1 mg of talazoparib.

200 mg of the azabicyclo compound of Formula (I) or the salt thereof and 1.25 mg of talazoparib.

200 mg of the azabicyclo compound of Formula (I) or the salt thereof and 1.50 mg of talazoparib.

200 mg of the azabicyclo compound of Formula (I) or the salt thereof and 2 mg of talazoparib.

40 to 320 mg of the azabicyclo compound of Formula (I) or the salt thereof and 100 mg to 300 mg of niraparib.

40 to 200 mg of the azabicyclo compound of Formula (I) or the salt thereof and 100 mg of niraparib.

40 to 200 mg of the azabicyclo compound of Formula (I) or the salt thereof and 200 mg of niraparib.

40 to 200 mg of the azabicyclo compound of Formula (I) or the salt thereof and 300 mg of niraparib.

40 mg of the azabicyclo compound of Formula (I) or the salt thereof and 100 mg of niraparib.

40 mg of the azabicyclo compound of Formula (I) or the salt thereof and 200 mg of niraparib.

40 mg of the azabicyclo compound of Formula (I) or the salt thereof and 300 mg of niraparib.

80 mg of the azabicyclo compound of Formula (I) or the salt thereof and 100 mg of niraparib.

80 mg of the azabicyclo compound of Formula (I) or the salt thereof and 200 mg of niraparib.

80 mg of the azabicyclo compound of Formula (I) or the salt thereof and 300 mg of niraparib.

120 mg of the azabicyclo compound of Formula (I) or the salt thereof and 100 mg of niraparib.

120 mg of the azabicyclo compound of Formula (I) or the salt thereof and 200 mg of niraparib.

120 mg of the azabicyclo compound of Formula (I) or the salt thereof and 300 mg of niraparib.

160 mg of the azabicyclo compound of Formula (I) or the salt thereof and 100 mg of niraparib.

160 mg of the azabicyclo compound of Formula (I) or the salt thereof and 200 mg of niraparib.

160 mg of the azabicyclo compound of Formula (I) or the salt thereof and 300 mg of niraparib.

200 mg of the azabicyclo compound of Formula (I) or the salt thereof and 100 mg of niraparib.

200 mg of the azabicyclo compound of Formula (I) or the salt thereof and 200 mg of niraparib.

200 mg of the azabicyclo compound of Formula (I) or the salt thereof and 300 mg of niraparib.

40 to 320 mg of the azabicyclo compound of Formula (I) or the salt thereof and 200 mg to 800 mg of veliparib.

40 to 200 mg of the azabicyclo compound of Formula (I) or the salt thereof and 200 mg of veliparib.

40 to 200 mg of the azabicyclo compound of Formula (I) or the salt thereof and 300 mg of veliparib.

40 to 200 mg of the azabicyclo compound of Formula (I) or the salt thereof and 400 mg of veliparib.

40 to 200 mg of the azabicyclo compound of Formula (I) or the salt thereof and 500 mg of veliparib.

40 to 200 mg of the azabicyclo compound of Formula (I) or the salt thereof and 600 mg of veliparib.

40 to 200 mg of the azabicyclo compound of Formula (I) or the salt thereof and 700 mg of veliparib.

40 to 200 mg of the azabicyclo compound of Formula (I) or the salt thereof and 800 mg of veliparib.

40 mg of the azabicyclo compound of Formula (I) or the salt thereof and 200 mg of veliparib.

40 mg of the azabicyclo compound of Formula (I) or the salt thereof and 300 mg of veliparib.

40 mg of the azabicyclo compound of Formula (I) or the salt thereof and 400 mg of veliparib.

40 mg of the azabicyclo compound of Formula (I) or the salt thereof and 500 mg of veliparib.

40 mg of the azabicyclo compound of Formula (I) or the salt thereof and 600 mg of veliparib.

40 mg of the azabicyclo compound of Formula (I) or the salt thereof and 700 mg of veliparib.

40 mg of the azabicyclo compound of Formula (I) or the salt thereof and 800 mg of veliparib.

80 mg of the azabicyclo compound of Formula (I) or the salt thereof and 200 mg of veliparib.

80 mg of the azabicyclo compound of Formula (I) or the salt thereof and 300 mg of veliparib.

80 mg of the azabicyclo compound of Formula (I) or the salt thereof and 400 mg of veliparib.

80 mg of the azabicyclo compound of Formula (I) or the salt thereof and 500 mg of veliparib.

80 mg of the azabicyclo compound of Formula (I) or the salt thereof and 600 mg of veliparib.

80 mg of the azabicyclo compound of Formula (I) or the salt thereof and 700 mg of veliparib.

80 mg of the azabicyclo compound of Formula (I) or the salt thereof and 800 mg of veliparib.

120 mg of the azabicyclo compound of Formula (I) or the salt thereof and 200 mg of veliparib.

120 mg of the azabicyclo compound of Formula (I) or the salt thereof and 300 mg of veliparib.

120 mg of the azabicyclo compound of Formula (I) or the salt thereof and 400 mg of veliparib.

120 mg of the azabicyclo compound of Formula (I) or the salt thereof and 500 mg of veliparib.

120 mg of the azabicyclo compound of Formula (I) or the salt thereof and 600 mg of veliparib.

120 mg of the azabicyclo compound of Formula (I) or the salt thereof and 700 mg of veliparib.

120 mg of the azabicyclo compound of Formula (I) or the salt thereof and 800 mg of veliparib.

160 mg of the azabicyclo compound of Formula (I) or the salt thereof and 200 mg of veliparib.

160 mg of the azabicyclo compound of Formula (I) or the salt thereof and 300 mg of veliparib.

160 mg of the azabicyclo compound of Formula (I) or the salt thereof and 400 mg of veliparib.

160 mg of the azabicyclo compound of Formula (I) or the salt thereof and 500 mg of veliparib.

160 mg of the azabicyclo compound of Formula (I) or the salt thereof and 600 mg of veliparib.

160 mg of the azabicyclo compound of Formula (I) or the salt thereof and 700 mg of veliparib.

160 mg of the azabicyclo compound of Formula (I) or the salt thereof and 800 mg of veliparib.

200 mg of the azabicyclo compound of Formula (I) or the salt thereof and 200 mg of veliparib.

200 mg of the azabicyclo compound of Formula (I) or the salt thereof and 300 mg of veliparib.

200 mg of the azabicyclo compound of Formula (I) or the salt thereof and 400 mg of veliparib.

200 mg of the azabicyclo compound of Formula (I) or the salt thereof and 500 mg of veliparib.

200 mg of the azabicyclo compound of Formula (I) or the salt thereof and 600 mg of veliparib.

200 mg of the azabicyclo compound of Formula (I) or the salt thereof and 700 mg of veliparib.

200 mg of the azabicyclo compound of Formula (I) or the salt thereof and 800 mg of veliparib.

The tumors intended in the present invention are not particularly limited as long as they fall within a range in which a potentiating effect on an antitumor effect is exerted. The tumors are preferably tumors on which the azabicyclo compound of Formula (I) or a salt thereof exert an antitumor effect, more preferably malignant tumors involving Hsp90.

Specific examples of the cancers targeted by the antitumor agent of the present invention include head and neck cancer, digestive organ cancer (for example, esophageal cancer, stomach cancer, duodenal cancer, liver cancer, biliary tract cancer (for example, gallbladder/bile duct cancer), pancreatic cancer, small intestinal cancer, large intestine cancer (for example, colorectal cancer, colon cancer, or rectal cancer)), lung cancer (for example, non-small cell lung cancer or small cell lung cancer), breast cancer, ovarian cancer, uterus cancer (for example, cervical cancer or uterine corpus cancer), kidney cancer, bladder cancer, prostate cancer, skin cancer (for example, malignant melanoma or epidermal cancer), blood cancer (for example, multiple myeloma or acute myeloid leukemia), and sarcoma (for example, osteosarcoma, soft tissue sarcoma, uterine sarcoma, or gastrointestinal stromal tumor). Among them, digestive organ cancer, lung cancer, breast cancer, ovarian cancer, uterus cancer, prostate cancer, skin cancer, sarcoma, or blood cancer is preferable, and colorectal cancer, pancreatic cancer, lung cancer, breast cancer, ovarian cancer, uterus cancer, prostate cancer, gallbladder cancer, stomach cancer, skin cancer, sarcoma, or blood cancer is more preferable, from the viewpoint of a synergistic action on an antitumor effect when the azabicyclo compound of the present invention or a salt thereof is used in combination. Pancreatic cancer, breast cancer, ovarian cancer, uterus cancer, or prostate cancer is further preferable. Herein, the cancer includes not only primary tumor but also cancer metastasizing to other organ(s) (for example, liver).

In the present invention, the "treatment" includes postoperative adjuvant chemotherapy which is performed for prevention of recurrence after a tumor is removed surgically, and preoperative adjuvant chemotherapy which is preliminarily performed for surgically removing a tumor.

In the present invention, the azabicyclo compound of Formula (I) or a salt thereof and the PARP inhibitor may be formulated into a plurality of dosage forms as the respective dosage forms of the active ingredients or may be formulated into one dosage form (i.e., formulated as a combination drug), on the basis of the respective administration forms or schedules of administration of the active ingredients. Their respective formulations may be produced and sold in one package suitable for use in combination or may be produced and sold in separate packages.

The administration forms of the antitumor agent of the present invention are not particularly limited, and can be appropriately selected in accordance with the therapeutic purpose. Specific examples of the administration form include oral agents (for examples, tablets, coated tablets, powder, granules, capsules, and liquid), injections, suppositories, cataplasms, and ointments. Oral agents are preferable.

Such formulations in various dosage forms can be prepared by a usual known method by use of a pharmaceutically acceptable carrier, if necessary. Such a carrier can be selected from the group consisting of a variety of carriers generally employed in pharmaceuticals, and examples thereof include an excipient, a binder, a disintegrant, a lubricant, a diluent, a solubilizing agent, a suspending agent, a tonicity agent, a pH-adjusting agent, a buffer, a stabilizer, a coloring agent, a flavoring agent, and a deodorant.

The present invention also relates to an antitumor effect potentiator comprising as an active ingredient an azabicyclo compound of Formula (I) or a salt thereof for potentiating an antitumor effect of a PARP inhibitor on a cancer patient. The antitumor effect potentiator has the formulation form of the antitumor agent described above.

The present invention also relates to an antitumor agent comprising an azabicyclo compound of Formula (I) or a salt thereof for treating a cancer patient given a PARP inhibitor. The antitumor agent has the formulation form described above.

The present invention also relates to a kit formulation comprising an azabicyclo compound of Formula (I) or a salt thereof, and an instruction manual stating that the azabicyclo compound of Formula (I) or the salt thereof and a PARP inhibitor are administered in combination to a cancer patient.

Herein, the "instruction manual" may state the dosage described above and preferably recommends the dosage described above, irrespective of the presence or absence of legal binding power. Specific examples thereof include package inserts and pamphlets. The kit formulation comprising the instruction manual may be a kit formulation in which the instruction manual is printed or attached to a package, or may be a kit formulation in which the instruction manual is enclosed, together with the antitumor agent, in a package.

EXAMPLES

Hereinafter, the present invention will be described in more detail by means of Examples, which should not be construed as limiting the invention. Many modifications can be made by a person having ordinary knowledge in the field of the invention without departing from the technical idea of the invention.

Example 1: In Vitro Combination Analysis of Compound 1 and Olaparib a Material and Method A human pancreatic cancer cell line Capan-1 (American Type Culture Collection, ATCC) in McCoy's 5A medium (Thermo Scientific) containing 10% fetal bovine serum (Sigma-Aldrich), human breast cancer cell lines HCC38, HCC1395, and HCC1428 (ATCC) in RPMI-1640 medium (Wako Pure Chemical Industries, Ltd.) containing 10% fetal bovine serum, a human breast cancer cell line Hs578T (European Collection of Cell Cultures) in D-MEM medium (Wako Pure Chemical Industries, Ltd.) containing 10% fetal bovine serum and 10 μg/mL bovine insulin, and a human breast cancer cell line MCF7 in MEM medium (Nacalai Tesque, Inc.) containing 10% fetal bovine serum, 0.1 mM NEAA, and 1 mM sodium pyruvate were allowed to proliferate. All the cells were maintained at 37° C. under 5% $CO_2$ and subcultured once or twice per week at a ratio from 1:2 to 1:10.

Cell Survival Rate Assay

Cell survival rates were measured by using CellTiter-Glo. The cells were recovered by a routine method, suspended in their respective media, and seeded in 96-well plates. The numbers of cells to be seeded were 200 cells/50 μL (Hs578T), 1,000 cells/50 μL (MCF7), 2,000 cells/50 μL (Capan-1 and HCC1428), and 4,000 cells/50 μL (HCC38 and HCC1395) per well. After incubation at 37° C. for 24 hours under 5% CO2, 50 μL of a medium containing olaparib and Compound 1 or Vehicle (DMSO) was added to each well. For Capan-1, HCC1428, and MCF7, the concentrations of olaparib were nine concentrations, 1, 3, 10, 30, 100, 300, 1,000, 3,000, and 10,000 nM, and zero (DMSO), and the concentrations of Compound 1 were five concentrations, 100, 300, 1,000, 3,000, and 10,000 nM, and zero (DMSO). All of 60 combinations in total thereof were studied. Two wells were assigned to each combination. For HCC38, HCC1395, and Hs578T, the concentrations of olaparib were four concentrations, 1,000, 3,000, 10,000, and 30,000 nM, and zero (DMSO), and the concentrations of Compound 1 were five concentrations, 100, 300, 1,000, 3,000, and 10,000 nM, and zero (DMSO). All of 30 combinations in total thereof were studied. Four wells were assigned to each combination.

The plates were further incubated at 37° C. for 72 hours (Hs578T) or 168 hours (Capan-1, HCC38, HCC1395, HCC1428, and MCF7) under 5% $CO_2$. 100 μL of CellTiter-Glo solution was added per well, and the plates were incubated at room temperature for 10 minutes, followed by the measurement of chemiluminescence by using plate reader Enspire. A mean of each combination was calculated from the obtained data, and cell survival rates normalized against a control supplemented with a medium containing Vehicle were calculated. Fa (fraction of affect) values were calculated by subtracting 1 from the cell survival rates.

The half maximal inhibitory concentration (IC50) of each pharmaceutical was determined by using median effect analytical software CalcuSyn 2.0 (CalcuSyn, Inc.). Subsequently, a combination index (CI) was determined for the concentrations of the pharmaceuticals in each combination. CI of more than 1, equal to 1, or less than 1 indicates antagonistic, additive, or synergistic action, respectively (Table 1) (Pharmacol Rev. 2006; 58 (3): 621-81; BMC Complement Altern Med. 2013; 13: 212; and Anticancer Res. 2005; 25 (3B): 1909-17).

TABLE 1

[(Description of combination index value)

| Range of CI (upper limit) | Description |
|---|---|
| 0.1 | Very strong synergistic action |
| 0.3 | Strong synergistic action |
| 0.7 | Synergistic action |
| 0.85 | Moderate synergistic action |
| 0.9 | Slight synergistic action |
| 1 | Almost additive |
| 1.2 | Slight antagonistic action |
| 1.45 | Moderate antagonistic action |
| 3.3 | Antagonistic action |
| 10 | Strong antagonistic action |
| >10 | Very strong antagonistic action |

It is considered that Fa values closer to 1 indicate a concentration range in which pharmaceutical effects are too strong while Fa values closer to 0 indicate a concentration range in which pharmaceutical effects are too weak. Since these are not appropriate for discussing synergistic effects, combinations of the concentrations of both the pharmaceuticals which attained 0.2 Fa 0.8 were extracted from the Fa values calculated from all the 30 combinations of the concentrations of Compound 1 and olaparib for each cell, and subjected to linear curve fitting by CalcuSyn to obtain CI.

B Results

The obtained CI and the concentrations of both the pharmaceuticals which provided it were studied to find the respective concentration ranges of the pharmaceuticals which attained CI of moderate or greater synergistic action (less than 0.85) (Table 2).

TABLE 2

| Cell line | Compound 1 concentration (nM) | Olaparib concentration (nM) | Fa value | CI | | Combination ratio |
|---|---|---|---|---|---|---|
| HCC38 | 300 | 10000 | 0.7649 | 0.356 | Synergistic action | 1:33.333 |
| HCC38 | 300 | 30000 | 0.8295 | 0.428 | Synergistic action | 1:100 |
| HCC1395 | 300 | 300 | 0.8306 | 0.164 | Strong synergistic action | 1:1 |
| HCC1395 | 300 | 1000 | 0.8575 | 0.214 | Strong synergistic action | 1:3.333 |
| Hs578T | 300 | 3000 | 0.5296 | 0.571 | Synergistic action | 1:10 |
| Hs578T | 300 | 10000 | 0.7498 | 0.276 | Strong synergistic action | 1:33.333 |
| Hs578T | 1000 | 10000 | 0.7694 | 0.466 | Synergistic action | 1:10 |
| Capan-1 | 300 | 300 | 0.532 | 0.745 | Moderate synergistic action | 1:1 |
| Capan-1 | 300 | 1000 | 0.591 | 0.697 | Synergistic action | 1:3.333 |
| HCC1428 | 300 | 3000 | 0.763 | 0.453 | Synergistic action | 1:10 |
| HCC1428 | 300 | 10000 | 0.796 | 0.406 | Synergistic action | 1:33.333 |
| MCF7 | 300 | 1000 | 0.756 | 0.432 | Synergistic action | 1:3.33 |
| MCF7 | 300 | 3000 | 0.828 | 0.591 | Synergistic action | 1:10 |

For the HCC38 cells, a combination which exhibited synergistic action was found in Compound 1 at a concentration of 300 nM and olaparib at concentrations of 10,000 and 30,000 nM.

For the HCC1395 cells, a combination which exhibited strong synergistic action was found in Compound 1 at a concentration of 300 nM and olaparib at concentrations of 300 or 1,000 nM.

For the Hs578T cells, a combination which exhibited synergistic action was found in Compound 1 at concentrations of 300 and 1,000 nM and olaparib at concentrations of 3,000 and 10,000 nM, and among them, strong synergistic action was found in 300 nM Compound 1 and 10,000 nM olaparib.

For the Capan-1 cells, moderate synergistic action was found in Compound 1 at a concentration of 300 nM and olaparib at a concentration of 300 nM, and synergistic action was found in Compound 1 at a concentration of 300 nM and olaparib at a concentration of 1,000 nM.

For the HCC1428 cells, a combination which exhibited synergistic action was found in Compound 1 at a concentration of 300 nM and olaparib at concentrations of 3,000 and 10,000 nM.

For the MCF7 cells, a combination which exhibited synergistic action was found in Compound 1 at a concentration of 300 nM and olaparib at concentrations of 1,000 and 3,000 nM.

Example 2: In Vitro Combination Analysis of Compound 1 and Rucaparib

Combinations of Compound 1 and rucaparib for cell lines other than those described above were also subjected to the same in vitro combination analysis as above. As shown in Table 3, the combinations of Compound 1 and rucaparib exhibited synergistic action (CI<0.7). Results obtained by using an HCC1395 cell line showed a strong synergistic effect (CI<0.30) in one or more combinations of concentrations.

TABLE 3

| Cell line | Compound 1 concentration (nM) | Rucaparib concentration (nM) | Fa value | CI | | Combination ratio |
|---|---|---|---|---|---|---|
| HCC38 | 300 | 3000 | 0.5495 | 0.797 | Moderate synergistic action | 1:10 |
| HCC38 | 300 | 10000 | 0.6248 | 0.769 | Moderate synergistic action | 1:33.3333 |
| HCC1395 | 300 | 300 | 0.8361 | 0.109 | Strong synergistic action | 1:1 |
| HCC1395 | 300 | 1000 | 0.8559 | 0.118 | Strong synergistic action | 1:3.3333 |
| HCC1395 | 300 | 3000 | 0.8647 | 0.172 | Strong synergistic action | 1:10 |
| Hs578T | 300 | 30000 | 0.7903 | 0.675 | Synergistic action | 1:100 |
| Hs578T | 1000 | 30000 | 0.843 | 0.616 | Synergistic action | 1:30 |
| Hs578T | 3000 | 30000 | 0.8846 | 0.662 | Synergistic action | 1:10 |
| Capan-1 | 300 | 300 | 0.496 | 0.668 | Synergistic action | 1:1 |
| Capan-1 | 300 | 1000 | 0.594 | 0.492 | Synergistic action | 1:3.3333 |
| Capan-1 | 300 | 3000 | 0.571 | 0.672 | Synergistic action | 1:10 |
| MCF7 | 300 | 1000 | 0.702 | 0.492 | Synergistic action | 1:3.3333 |
| MCF7 | 300 | 3000 | 0.786 | 0.546 | Synergistic action | 1:10 |
| HCC1428 | 300 | 3000 | 0.674 | 0.518 | Synergistic action | 1:10 |
| HCC1428 | 300 | 10000 | 0.673 | 0.722 | Moderate synergistic action | 1:33.3333 |

As described above, the azabicyclo compound of Formula (I) of the present invention or a salt thereof was found to exhibit strong synergistic action by use in combination with the PARP inhibitor.

The invention claimed is:

1. A method for treating cancer, comprising:

administering to a patient in need thereof a combination therapy for a dosing period comprising one week, the combination therapy comprising:

a dosage of 80 mg per day of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide, or a salt thereof, administered for five consecutive days each week followed by a 2-day drug holiday during the dosing period; and a dosage of 200 mg per day of niraparib administered every day of the dosing period.

2. The method of claim 1, wherein the dosage of 80 mg per day of 3-ethyl-4-(3-isopropyl-4-(4-(1-methyl-1H-pyrazol-4-yl)-1H-imidazol-1-yl-1H-pyrazolo[3,4-b]pyridin-1-yl}benzamide, or a salt thereof, and the dosage of 200 mg per day of niraparib are administered concurrently.

3. The method of claim 1, wherein the dosage of 80 mg per day of 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide, or a salt thereof, and the dosage of 200 mg per day of niraparib are administered separately in a staggered manner.

4. The method of claim 1, wherein the cancer comprises a primary pancreatic cancer, breast cancer, ovarian cancer, uterus cancer, prostate cancer, bladder cancer, or uterine sarcoma.

5. The method of claim 1, wherein the one week dosing period is repeated.

* * * * *